(12) United States Patent
Doyle et al.

(10) Patent No.: US 12,004,717 B2
(45) Date of Patent: Jun. 11, 2024

(54) ENDOSCOPE WITH DETACHABLE CAMERA MODULE

(71) Applicant: GYRUS ACMI, INC., Southborough, MA (US)

(72) Inventors: Philip J. Doyle, Center Valley, PA (US); Nikhil M. Murdeshwar, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 316 days.

(21) Appl. No.: 17/126,965

(22) Filed: Dec. 18, 2020

(65) Prior Publication Data

US 2021/0186307 A1    Jun. 24, 2021

Related U.S. Application Data

(60) Provisional application No. 63/031,316, filed on May 28, 2020, provisional application No. 63/031,312, (Continued)

(51) Int. Cl.
*A61B 1/018* (2006.01)
*A61B 1/00* (2006.01)
(Continued)

(52) U.S. Cl.
CPC .......... *A61B 1/018* (2013.01); *A61B 1/00006* (2013.01); *A61B 1/00029* (2013.01);
(Continued)

(58) Field of Classification Search
CPC ..... A61B 1/00105; A61B 1/041; A61B 1/018; A61B 1/00042; A61B 1/00029;
(Continued)

(56) References Cited

U.S. PATENT DOCUMENTS 4,660,982 A * 4/1987 Okada ................ A61B 1/00101
356/636
4,862,872 A * 9/1989 Yabe .................. A61B 1/00057
600/133
(Continued)

FOREIGN PATENT DOCUMENTS

CA    2798716 A1    6/2013
CA    3068554 A1    1/2019
(Continued)

OTHER PUBLICATIONS

"U.S. Appl. No. 17/241,212, Preliminary Amendment filed Apr. 27, 2021", 6 pgs.
(Continued)

*Primary Examiner* — Michael J Carey
*Assistant Examiner* — Megan Elizabeth Monahan
(74) *Attorney, Agent, or Firm* — Schwegman Lundberg & Woessner, P.A.

(57) ABSTRACT

A modular endoscope system comprises a first modular section comprising imaging and illumination units, and a patient-insertable second modular section that can be detached to the first modular section via an attachment mechanism, wherein the first modular section is positionable at a distal end section of the second modular section and is configured to illuminate and image a portion of a patient anatomy. A method of using a modular endoscopy system comprises attaching a first modular section of the modular endoscopy system to a second modular section of the modular endoscopy system, positioning at least a portion of the modular endoscopy system within a patient, illuminating and imaging a portion of a patient anatomy via the first modular section, removing the modular endoscopy system from the patient, and detaching the second modular section
(Continued)

from the first modular section after removal of the modular endoscopy system from the patient.

23 Claims, 17 Drawing Sheets

Related U.S. Application Data filed on May 28, 2020, provisional application No. 62/951,157, filed on Dec. 20, 2019.

(51) Int. Cl.
| | |
|---|---|
| *A61B 1/005* | (2006.01) |
| *A61B 1/05* | (2006.01) |
| *A61B 1/06* | (2006.01) |
| *A61B 1/12* | (2006.01) |
| *A61B 90/00* | (2016.01) |
| *A61L 2/10* | (2006.01) |
| *A61L 2/18* | (2006.01) |
| *A61B 1/04* | (2006.01) |

(52) U.S. Cl.
CPC ...... *A61B 1/00034* (2013.01); *A61B 1/00039* (2013.01); *A61B 1/00042* (2022.02); *A61B 1/00062* (2013.01); *A61B 1/00085* (2013.01); *A61B 1/00101* (2013.01); *A61B 1/00105* (2013.01); *A61B 1/00124* (2013.01); *A61B 1/0014* (2013.01); *A61B 1/0052* (2013.01); *A61B 1/0055* (2013.01); *A61B 1/0057* (2013.01); *A61B 1/05* (2013.01); *A61B 1/0676* (2013.01); *A61B 1/121* (2013.01); *A61B 1/126* (2013.01); *A61B 90/06* (2016.02); *A61L 2/10* (2013.01); *A61L 2/18* (2013.01); *A61B 1/00009* (2013.01); *A61B 1/044* (2022.02); *A61B 2090/064* (2016.02); *A61B 2560/0475* (2013.01); *A61B 2560/0487* (2013.01); *A61L 2202/24* (2013.01)

(58) Field of Classification Search
CPC ............ A61B 1/00034; A61B 1/00101; A61B 1/0008; A61B 1/00006; A61B 1/00062; A61B 1/00085; A61B 1/00124; A61B 1/0014; A61B 1/0052; A61B 1/0055; A61B 1/0057; A61B 1/05; A61B 1/0676; A61B 1/121; A61B 1/126; A61B 1/00009
See application file for complete search history.

(56) References Cited

U.S. PATENT DOCUMENTS

| | | | | |
|---|---|---|---|---|
| 5,193,525 | A * | 3/1993 | Silverstein | A61B 1/00096 |
| | | | | 600/920 |
| 5,489,256 | A | 2/1996 | Adair | |
| 6,459,926 | B1 | 10/2002 | Nowlin et al. | |
| 8,608,649 | B2 | 12/2013 | Mcweeney et al. | |
| 9,198,719 | B2 | 12/2015 | Murdeshwar et al. | |
| 11,445,890 | B2 * | 9/2022 | Levinson | A61B 1/00131 |
| 2002/0165444 | A1 * | 11/2002 | Whitman | A61B 1/0607 |
| | | | | 600/407 |
| 2003/0073955 | A1 * | 4/2003 | Otawara | A61B 1/00098 |
| | | | | 600/101 |
| 2006/0149127 | A1 | 7/2006 | Seddiqui et al. | |
| 2006/0217594 | A1 * | 9/2006 | Ferguson | A61B 1/00105 |
| | | | | 600/179 |
| 2007/0173695 | A1 | 7/2007 | Hirata | |
| 2008/0091065 | A1 * | 4/2008 | Oshima | H04N 19/60 |
| | | | | 382/128 |
| 2011/0245602 | A1 | 10/2011 | Brannon | |
| 2011/0313428 | A1 | 12/2011 | Mohr et al. | |
| 2012/0232345 | A1 | 9/2012 | Levy et al. | |
| 2014/0187856 | A1 | 7/2014 | Holoien et al. | |
| 2014/0276101 | A1 | 9/2014 | Asselin et al. | |
| 2015/0031946 | A1 | 1/2015 | Saadat et al. | |
| 2015/0031947 | A1 | 1/2015 | Kudo et al. | |
| 2016/0235279 | A1 | 8/2016 | Yamakawa | |
| 2017/0056102 | A1 | 3/2017 | Germain et al. | |
| 2017/0135560 | A1 | 5/2017 | Elia et al. | |
| 2017/0224194 | A1 | 8/2017 | Fujitani et al. | |
| 2017/0280975 | A1 * | 10/2017 | Levy | A61B 1/00105 |
| 2017/0325669 | A1 | 11/2017 | Levy | |
| 2018/0160888 | A1 * | 6/2018 | Bunch | A61B 1/3132 |
| 2018/0235440 | A1 | 8/2018 | Okamoto | |
| 2019/0059703 | A1 | 2/2019 | Ting | |
| 2021/0093166 | A1 | 4/2021 | Shin et al. | |
| 2021/0196110 | A1 | 7/2021 | Uram | |
| 2021/0338045 | A1 | 11/2021 | Crowley et al. | |
| 2022/0240760 | A1 | 8/2022 | Zhang | |

FOREIGN PATENT DOCUMENTS

| | | |
|---|---|---|
| CN | 114845619 A | 8/2022 |
| CN | 115734739 A | 3/2023 |
| EP | 1302151 B1 | 5/2005 |
| EP | 3245930 A1 | 11/2017 |
| JP | 2745233 B2 | 4/1998 |
| JP | 2746651 B2 | 5/1998 |
| JP | 2750612 B2 | 5/1998 |
| JP | 2750613 B2 | 5/1998 |
| JP | 2758435 B2 | 5/1998 |
| JP | 2787471 B2 | 8/1998 |
| JP | 2802952 B2 | 9/1998 |
| JP | 2813366 B2 | 10/1998 |
| JP | 2842698 B2 | 1/1999 |
| JP | 3207991 B2 | 9/2001 |
| JP | 3220580 B2 | 10/2001 |
| JP | 4081259 B2 | 10/2001 |
| JP | 3228618 B2 | 11/2001 |
| JP | 3230617 B2 | 11/2001 |
| JP | 3327976 B2 | 2/2002 |
| JP | 3271826 B2 | 4/2002 |
| JP | 3273071 B2 | 4/2002 |
| JP | 3274746 B2 | 4/2002 |
| JP | 3276712 B2 | 4/2002 |
| JP | 3283100 B2 | 5/2002 |
| JP | 3290006 B2 | 6/2002 |
| JP | 3304161 B2 | 7/2002 |
| JP | 3306155 B2 | 7/2002 |
| JP | 3325103 B2 | 9/2002 |
| JP | 3328044 B2 | 9/2002 |
| JP | 3349804 B2 | 9/2002 |
| JP | 3353934 B2 | 9/2002 |
| JP | 3335241 B2 | 10/2002 |
| JP | 3342140 B2 | 11/2002 |
| JP | 3349813 B2 | 11/2002 |
| JP | 3365861 B2 | 11/2002 |
| JP | 3368616 B2 | 11/2002 |
| JP | 3371385 B2 | 11/2002 |
| JP | 3376121 B2 | 11/2002 |
| JP | 3352220 B2 | 12/2002 |
| JP | 3352221 B2 | 12/2002 |
| JP | 3353932 B2 | 12/2002 |
| JP | 3379714 B2 | 12/2002 |
| JP | 3365820 B2 | 1/2003 |
| JP | 3365857 B2 | 1/2003 |
| JP | 3368569 B2 | 1/2003 |
| JP | 3387594 B2 | 1/2003 |
| JP | 3394607 B2 | 1/2003 |
| JP | 3394608 B2 | 1/2003 |
| JP | 3376076 B2 | 2/2003 |
| JP | 3376106 B2 | 2/2003 |
| JP | 3392923 B2 | 3/2003 |
| JP | 3394617 B2 | 4/2003 |
| JP | 3394633 B2 | 4/2003 |
| JP | 3402646 B2 | 5/2003 |
| JP | 3433996 B2 | 5/2003 |
| JP | 3421038 B2 | 6/2003 |
| JP | 3431374 B2 | 7/2003 |
| JP | 3450510 B2 | 7/2003 |

(56) References Cited

FOREIGN PATENT DOCUMENTS

| | | |
|---|---|---|
| JP | 3476964 B2 | 9/2003 |
| JP | 3485196 B2 | 10/2003 |
| JP | 3485648 B2 | 1/2004 |
| JP | 3485662 B2 | 1/2004 |
| JP | 3485663 B2 | 1/2004 |
| JP | 3490540 B2 | 1/2004 |
| JP | 3497591 B2 | 2/2004 |
| JP | 3510327 B2 | 3/2004 |
| JP | 3514820 B2 | 3/2004 |
| JP | 3514840 B2 | 3/2004 |
| JP | 3514847 B2 | 3/2004 |
| JP | 3514853 B2 | 3/2004 |
| JP | 3519823 B2 | 4/2004 |
| JP | 3523666 B2 | 4/2004 |
| JP | 3537180 B2 | 6/2004 |
| JP | 3540407 B2 | 7/2004 |
| JP | 3557280 B2 | 8/2004 |
| JP | 3597216 B2 | 12/2004 |
| JP | 3619554 B2 | 2/2005 |
| JP | 3651949 B2 | 5/2005 |
| JP | 2007289342 A | 11/2007 |
| JP | 4296159 B2 | 7/2009 |
| JP | 3196951 B2 | 3/2015 |
| JP | 3219521 B2 | 12/2018 |
| WO | WO-9315648 A1 | 8/1993 |
| WO | WO-2011140118 A1 | 11/2011 |
| WO | WO-2018189230 A1 | 10/2018 |
| WO | WO-2018221672 A1 | 12/2018 |
| WO | WO-2019152991 A1 | 8/2019 |
| WO | WO-2019203594 A1 | 10/2019 |
| WO | WO-2021127703 A2 | 6/2021 |
| WO | WO-2021127703 A3 | 7/2021 |
| WO | WO-2021222208 A1 | 11/2021 |

OTHER PUBLICATIONS

"International Application Serial No. PCT/US2020/070936, International Search Report dated Jun. 16, 2021", 8 pgs.

"International Application Serial No. PCT/US2020/070936, Invitation to Pay Additional Fees dated Apr. 21, 2021", 13 pgs.

"International Application Serial No. PCT/US2020/070936, Written Opinion dated Jun. 16, 2021", 11 pgs.

"International Application Serial No. PCT/US2021/029345, International Search Report dated Oct. 5, 2021", 9 pgs.

"International Application Serial No. PCT/US2021/029345, Invitation to Pay Additional Fees dated Aug. 11, 2021", 14 pgs.

"International Application Serial No. PCT/US2021/029345, Written Opinion dated Oct. 5, 2021", 12 pgs.

"U.S. Appl. No. 17/241,212, Restriction Requirement dated Oct. 13, 2022", 8 pgs.

"U.S. Appl. No. 17/241,212, Supplemental Preliminary Amendment filed Sep. 8, 2022", 7 pgs.

"International Application Serial No. PCT/US2020/070936, International Preliminary Report on Patentability dated Jun. 30, 2022", 13 pgs.

"International Application Serial No. PCT/US2021/029345, International Preliminary Report on Patentability dated Nov. 10, 2022", 14 pgs.

"U.S. Appl. No. 17/241,212, Examiner Interview Summary dated May 8, 2023", 2 pgs.

"U.S. Appl. No. 17/241,212, Non Final Office Action dated Feb. 17, 2023", 30 pgs.

"U.S. Appl. No. 17/241,212, Response filed May 17, 2023 to Non Final Office Action dated Feb. 17, 2023", 21 pgs.

"U.S. Appl. No. 17/241,212, Response filed Nov. 30, 2022 to Restriction Requirement dated Oct. 13, 2022", 9 pgs.

"Chinese Application Serial No. 202080088080.4, Voluntary Amendment filed Nov. 8, 2022", w/o English Claims, 8 pgs.

* cited by examiner

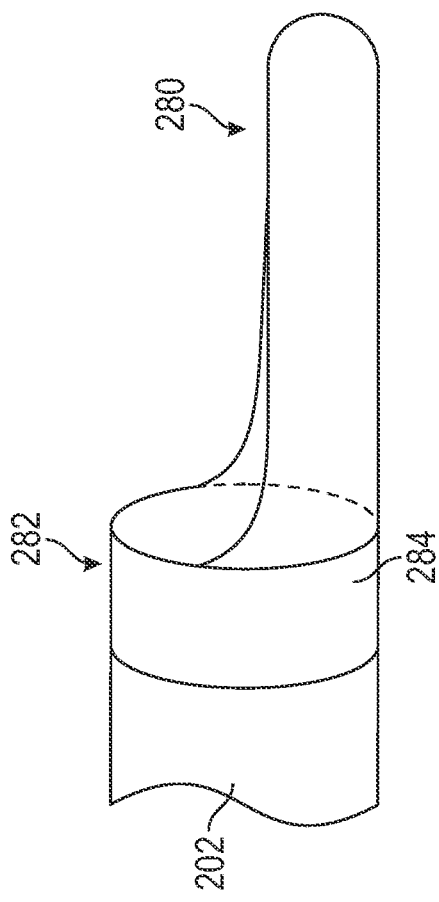
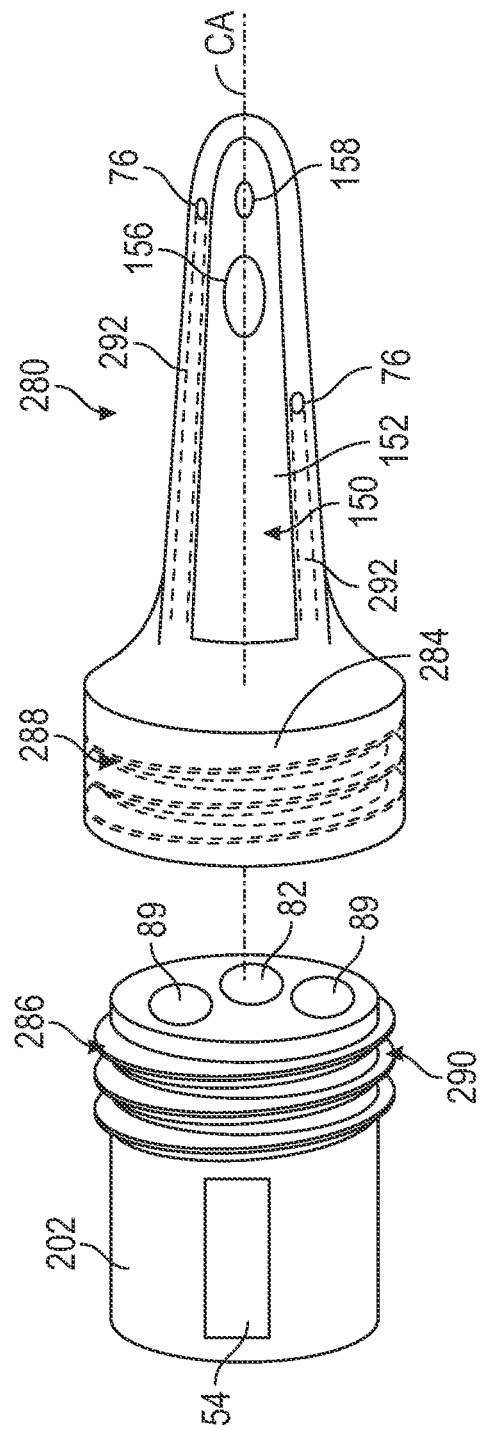
FIG. 12A
FIG. 12B

ENDOSCOPE WITH DETACHABLE CAMERA MODULE

CROSS-REFERENCE TO RELATED APPLICATIONS

This patent application claims the benefit of priority to U.S. Provisional Patent Application No. 62/951,157 filed Dec. 20, 2019 titled "MODULAR ENDOSCOPE WITH DETACHABLE AND SELECTIVELY DISPOSABLE COMPONENTS" and U.S. Provisional Patent Application No. 63/031,312 filed May 28, 2020 titled "ENDOSCOPE WITH DETACHABLE CAMERA MODULE" and U.S. Provisional Patent Application No. 63/031,316 filed May 28, 2020 titled "ENDOSCOPE WITH DETACHABLE HANDLE MODULE"; the entire contents of which are hereby incorporated by reference.

TECHNICAL FIELD

The present disclosure relates generally to medical devices comprising elongate bodies configured to be inserted into incisions or openings in anatomy of a patient to provide diagnostic or treatment operations.

More specifically, the present disclosure relates to endoscopes for imaging and/or providing passage of therapeutic devices toward various anatomical portions, including gastrointestinal tract (e.g., esophagus, stomach, duodenum, pancreaticobiliary duct, intestines, colon, and the like), renal area (e.g., kidney(s), ureter, bladder, urethra) and other internal organs (e.g., reproductive systems, sinus cavities, submucosal regions, respiratory tract), and the like.

BACKGROUND

Conventional endoscopes can be involved in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices for sampling or treating an anatomical region, and providing suction passageways for collecting fluids (e.g., saline or other preparations) and the like.

In conventional endoscopy, the distal portion of the endoscope can be configured for supporting and orienting a therapeutic device, such as with the use of an elevator. However, such distal portions can, in a few instances, lead to difficulty in sterilizing or reprocessing the distal portion after use. For example, conventional endoscopy devices can be completely reusable such that crevices between components or spaces within functional components of the distal portion can be difficult to access and clean.

SUMMARY

The present inventors have recognized that problems to be solved with conventional medical devices, and in particular endoscopes and duodenoscopes, include, among other things, particularly those that are difficult or not configured to be easily disassembled, 1) the need and difficulty of cleaning and sterilizing endoscopes after usage, 2) the cost of maintaining multiple endoscopes in inventory to perform different surgical techniques or therapeutic methods on different patients, and 3) the cost of purchasing medical devices having excess capacity or unwanted capabilities for a particular patient. The present disclosure can help provide solutions to these and other problems by providing systems, devices and methods for designing, building, using and deconstructing modular endoscopes. In particular, the present application is directed to attachment systems for detachable camera modules and detachable control modules for medical devices such as endoscopes and duodenoscopes. The camera modules and control modules can be configured for reuse after appropriate cleaning and sterilization, while the insertion sheaths and shafts to which they can be configured to connect can be configured for one-time use. As such, more expensive camera and control components can be modularly attached to inexpensive, disposable insertion sheaths and shafts. Said modular camera and control components can be configured for cleaning, e.g., by being encapsulated, while the insertion sheath and shafts can be inexpensively made to perform only the desired procedure and then disposed of after use. Such configurations can eliminate the need to clean in difficult to reach places in fully assembled devices and the need to maintain a large inventory of devices with different or excess capabilities.

The present inventors have also recognized that problems to be solved with conventional medical devices, and in particular endoscopes and duodenoscopes, include, among other things, the potential difficulty presented by having to attach modular components and the associated need to have attached modular components remain attached during a procedure. The present disclosure can help provide solutions to these and other problems by providing systems, devices and methods comprising attachment mechanisms for modular components, particularly modular imaging and illuminating units. The attachment systems described herein can facilitate simple and easy assembly such that, if needed, surgeons and other personnel can assemble the camera module to an insertion module in an operating room environment, yet can still provide adequate coupling to prevent unintended or accidental dislodgement of the camera module from the insertion module, such as when the insertion module is being used to insert the camera module into a patient.

The present inventors have additionally recognized that problems to be solved with conventional medical devices, and in particular endoscopes and duodenoscopes, include, among other things, the need for controlling endoscopes having different capabilities. In particular, modular endoscopes can be built with modular functional components that perform a wide variety of tasks, including different treatment options such as cutting, cauterizing, ablating and the like. As such, conventional endoscope control devices can be limited in accommodating additional functionality or adapting to modular accessories. The present disclosure can help provide solutions to these and other problems by providing systems, devices and methods comprising module control modules that can be coupled to proximal ends of insertion modules to control different functional modules attached to distal ends of the insertion modules. The control modules of the present disclosure can be provided with a wide variety of inputs, e.g., buttons, joysticks and touchscreens, that can be configured to control a variety of outputs.

In an example, a modular endoscope system can comprise a first modular section comprising an imaging unit and an illumination unit, and a second modular section that can be user-detachably connectable to the first modular section via an attachment mechanism, the second modular section being patient insertable, wherein the first modular section is positionable at a distal end section of the second modular section and is configured to illuminate and image a portion of a patient anatomy.

In another example, a method of using a modular endoscopy system can comprise attaching a first modular section of the modular endoscopy system to a second modular section of the modular endoscopy system, positioning at least a portion of the modular endoscopy system within a patient, illuminating and imaging a portion of a patient anatomy via the first modular section, removing the modular endoscopy system from the patient, and detaching the second modular section from the first modular section after removal of the modular endoscopy system from the patient.

In an additional example, an insertion section module for an endoscope can comprise a shaft comprising a flexible, elongate body extending from a proximal end to a distal end and a coupling mechanism located proximal the distal end, the coupling mechanism configured to releasably secure a camera module to the insertion section module.

In another example, a method of assembling a modular endoscopy system comprises bringing the first modular section of the modular endoscopy system proximate to a second modular section of the modular endoscopy system, the first modular section and the second modular section each comprising a near-field communication chip, establishing near-field communication between the first modular section and the second modular section when the first modular section and the second modular section are in a detached state, to validate the second modular section, and attaching the first modular section to the second modular section.

BRIEF DESCRIPTION OF DRAWINGS

FIG. 12A is a schematic illustration of a fifth example of an attachment mechanism for securing detachable camera modules of the present disclosure to a distal portion of the insertion section module of the modular endoscope of FIG. 5, the attachment mechanism comprising a screw-on holder.

FIG. 12B is a schematic illustration of the camera module of FIG. 6 coupled to the attachment mechanism of FIG. 12A, which is shown exploded form the insertion section module of the modular endoscope.

DETAILED DESCRIPTION

Figure 1:
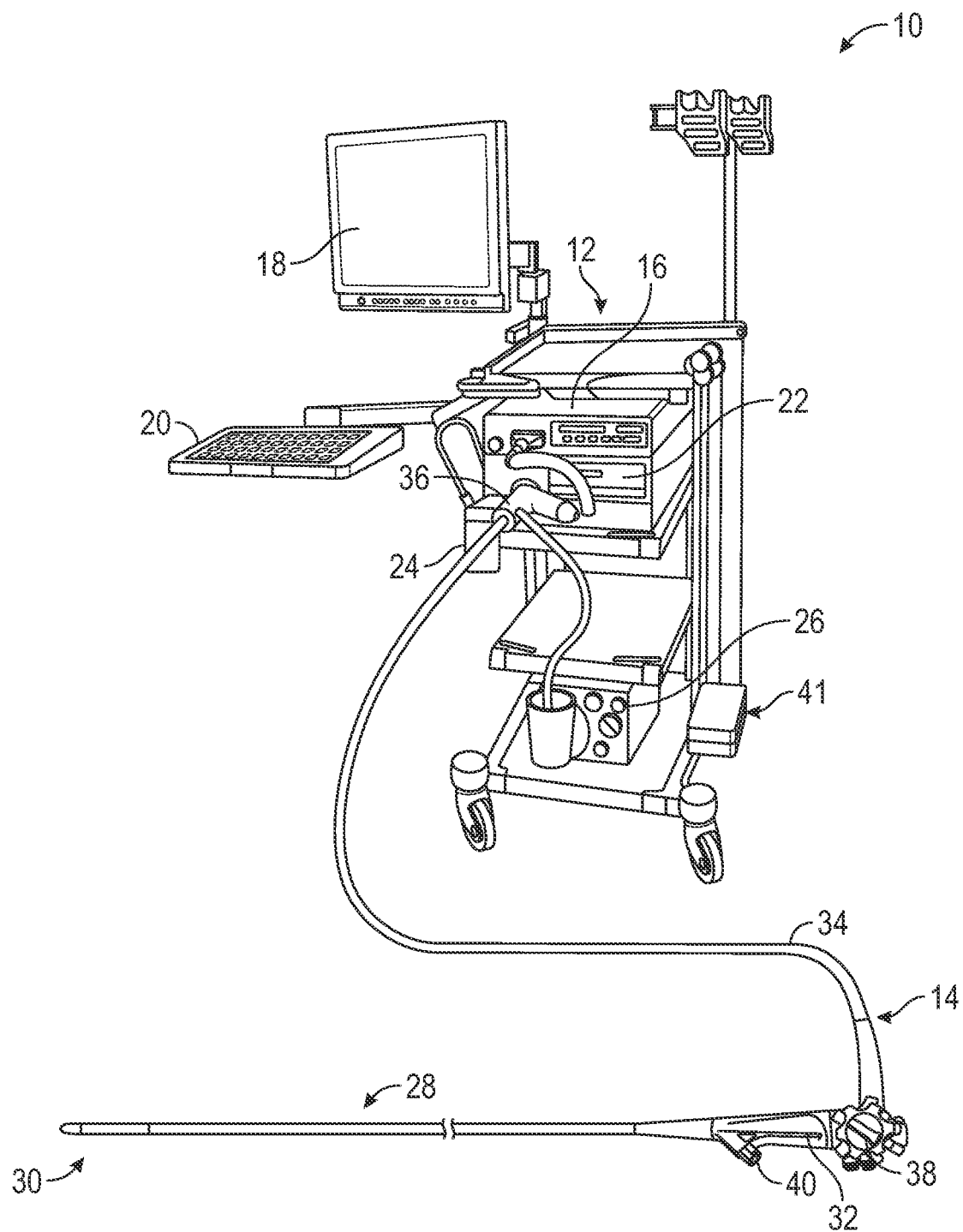
FIG. 1 is a schematic diagram of an endoscopy system comprising an imaging and control system and an endoscope, such as duodenoscope.

FIG. 1 is a schematic diagram of endoscopy system 10 comprising imaging and control system 12 and endoscope 14. The system of FIG. 1 is an illustrative example of an endoscopy system suitable for use with the systems, devices and methods described herein, such as modular endoscopy systems, modular endoscopes and methods for designing, building, using, deconstructing and reusing endoscope modules. According to some examples, endoscope 14 can be insertable into an anatomical region for imaging and/or to provide passage of one or more sampling devices for biopsies, or one or more therapeutic devices for treatment of a disease state associated with the anatomical region. Endoscope 14 can, in advantageous aspects, interface with and connect to imaging and control system 12. In the illustrated example, endoscope 14 comprises a duodenoscope, though other types of endoscopes can be used with the features and teachings of the present disclosure.

Imaging and control system 12 can comprise controller 16, output unit 18, input unit 20, light source 22, fluid source 24 and suction pump 26.

Imaging and control system 12 can include various ports for coupling with endoscopy system 10. For example, controller 16 can include a data input/output port for receiving data from and communicating data to endoscope 14. Light source 22 can include an output port for transmitting light to endoscope 14, such as via a fiber optic link. Fluid source 24 can include a port for transmitting fluid to endoscope 14. Fluid source 24 can comprise a pump and a tank of fluid or can be connected to an external tank, vessel or storage unit. Suction pump 26 can comprise a port used to draw a vacuum from endoscope 14 to generate suction, such as for withdrawing fluid from the anatomical region into which endoscope 14 is inserted. Output unit 18 and input unit 20 can be used by an operator of endoscopy system 10 to control functions of endoscopy system 10 and view output of endoscope 14. Controller 16 can additionally be used to generate signals or other outputs from treating the anatomical region into which endoscope 14 is inserted. In examples, controller 16 can generate electrical output, acoustic output, a fluid output and the like for treating the anatomical region with, for example, cauterizing, cutting, freezing and the like.

Endoscope 14 can comprise insertion section 28, functional section 30 and handle section 32, which can be coupled to cable section 34 and coupler section 36.

Insertion section 28 can extend distally from handle section 32 and cable section 34 can extend proximally from handle section 32. Insertion section 28 can be elongate and include a bending section, and a distal end to which functional section 30 can be attached. The bending section can be controllable (e.g., by control knob 38 on handle section 32) to maneuver the distal end through tortuous anatomical passageways (e.g., stomach, duodenum, kidney, ureter, etc.). Insertion section 28 can also include one or more working channels (e.g., an internal lumen) that can be elongate and support insertion of one or more therapeutic tools of functional section 30. The working channel can extend between handle section 32 and functional section 30. Additional functionalities, such as fluid passages, guide wires, and pull wires can also be provided by insertion section 28 (e.g., via suction or irrigation passageways, and the like).

Handle section 32 can comprise knob 38 as well as ports 40. Knob 38 can be coupled to a pull wire extending through insertion section 28. Ports 40 can be configured to couple various electrical cables, fluid tubes and the like to handle section 32 for coupling with insertion section 28.

Imaging and control system 12, according to examples, can be provided on a mobile platform (e.g., cart 41) with shelves for housing light source 22, suction pump 26, image processing unit 42, etc. Alternatively, several components of imaging and control system 12 shown in FIGS. 1 and 2 can be provided directly on endoscope 14 so as to make the endoscope "self-contained."

Figure 2:
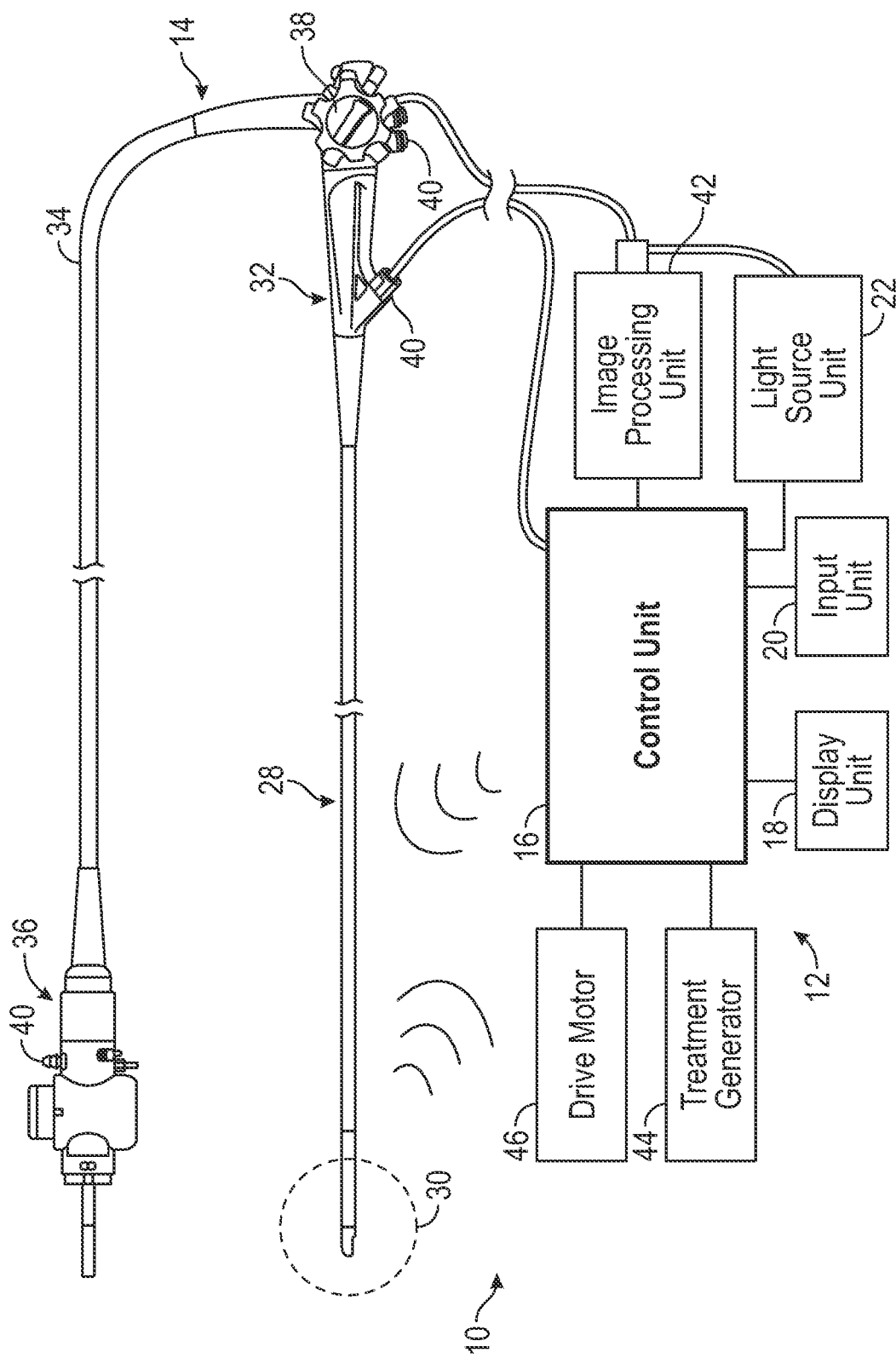
FIG. 2 is a schematic diagram of the endoscopy system of FIG. 1 comprising the endoscope connected to a control unit of the imaging and control system.

FIG. 2 is a schematic diagram of endoscopy system 10 of FIG. 1 comprising imaging and control system 12 and endoscope 14. FIG. 2 schematically illustrates components of imaging and control system 12 coupled to endoscope 14, which in the illustrated example comprises a duodenoscope. Imaging and control system 12 can comprise controller 16, which can include or be coupled to image processing unit 42, treatment generator 44 and drive unit 46, as well as light source 22, input unit 20 and output unit 18.

Image processing unit 42 and light source 22 can each interface with endoscope 14 by wired or wireless electrical connections. Imaging and control system 12 can accordingly illuminate an anatomical region, collect signals representing the anatomical region, process signals representing the anatomical region, and display images representing the anatomical region on display unit 18. Imaging and control system 12 can include light source 22 to illuminate the anatomical region using light of desired spectrum (e.g., broadband white light, narrow-band imaging using preferred electromagnetic wavelengths, and the like). Imaging and control system 12 can connect (e.g., via an endoscope connector) to endoscope 14 for signal transmission (e.g., light output from light source, video signals from imaging system in the distal end, and the like).

Fluid source 24 can comprise one or more sources of air, saline or other fluids, as well as associated fluid pathways (e.g., air channels, irrigation channels, suction channels) and connectors (barb fittings, fluid seals, valves and the like). Imaging and control system 12 can also include drive unit 46, which can be an optional component. Drive unit 46 can comprise a motorized drive for advancing a distal section of endoscope 14, as described in at least PCT Pub. No. WO 2011/140118 A1 to Frassica et al., titled "Rotate-to-Advance Catheterization System," which is hereby incorporated in its entirety by this reference.

Figure 3A:
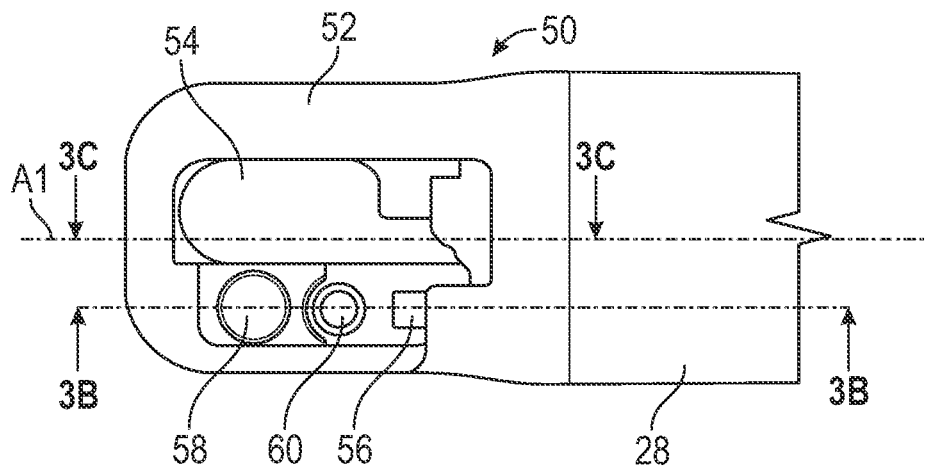
FIG. 3A is a schematic top view of a camera module including optical components for a side-viewing endoscope and an elevator mechanism.
Figure 3B:
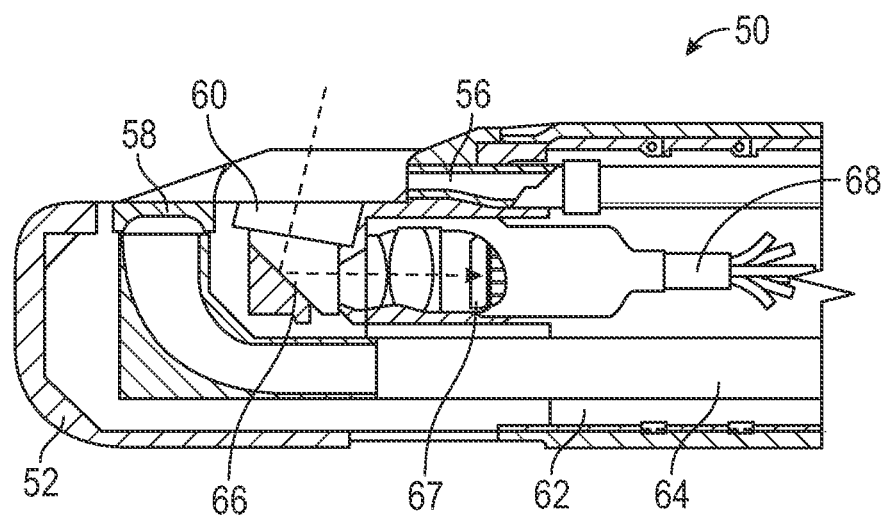
FIG. 3B is an enlarged cross-sectional view taken along the plane 3B-3B of FIG. 3A showing the optical components.
Figure 3C:
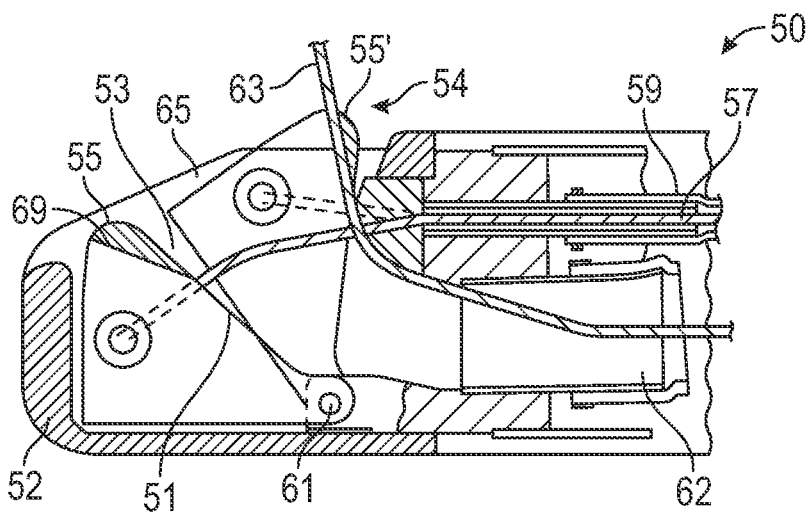
FIG. 3C is an enlarged cross-sectional view taken along the plane 3C-3C of FIG. 3A showing the elevator mechanism.

FIGS. 3A-3C illustrate a first example of functional section 30 of endoscope 14 of FIG. 2. FIG. 3A illustrates a top view of functional section 30 and FIG. 3B illustrates a cross-sectional view of functional section 30 taken along section plane 3B-3B of FIG. 3A. FIGS. 3A and 3B each illustrate "side-viewing endoscope" (e.g., duodenoscope) camera module 50. In side-viewing endoscope camera module 50, illumination and imaging systems are positioned such that the viewing angle of the imaging system corresponds to a target anatomy lateral to central longitudinal axis A1 of endoscope 14.

In the example of FIGS. 3A and 3B, side-viewing endoscope camera module 50 can comprise housing 52, elevator 54, fluid outlet 56, illumination lens 58 and objective lens 60. Housing 52 can form a fluid tight coupling with insertion section 28. Housing 52 can comprise opening for elevator 54. Elevator 54 can comprise a mechanism for moving a device inserted through insertion section 28. In particular, elevator 54 can comprise a device that can bend an elongate device extended through insertion section 28 along axis A1, as is discussed in greater detail with reference to FIG. 3C. Elevator 54 can be used to bend the elongate device at an angle to axis A1 to thereby treat the anatomical region adjacent side-viewing endoscope camera module 50. Elevator 54 is located alongside, e.g., radially outward of axis A1, illumination lens 58 and objective lens 60.

As can be seen in FIG. 3B, insertion section 28 can comprise central lumen 62 through which various components can be extended to connect functional section 30 with handle section 32 (FIG. 2). For example, illumination lens 58 can be connected to light transmitter 64, which can comprise a fiber optic cable or cable bundle extending to light source 22 (FIG. 1). Likewise, objective lens 60 can be coupled to prism 66 and imaging unit 67, which can be coupled to wiring 68. Also, fluid outlet 56 can be coupled to fluid line 69, which can comprise a tube extending to fluid source 24 (FIG. 1). Other elongate elements, e.g., tubes, wires, cables, can extend through lumen 62 to connect functional section 30 with components of endoscopy system 10, such as suction pump 26 (FIG. 1) and treatment generator 44 (FIG. 2).

FIG. 3C a schematic cross-sectional view taken along section plane 3C-3C of FIG. 30 showing an elevator 54. Elevator 54 can comprise deflector 55 that can be disposed in space 53 of housing 52. Deflector 55 can be connected to wire 57, which can extend through tube 59 to connect to handle section 32. Wire 57 can be actuated, such as by rotating a knob, pulling a lever, or pushing a button on handle section 32. Movement of wire 57 can cause rotation, e.g., clockwise, from a first position of deflector 55 about pin 61 to a second position of deflector 55, indicated by 55'. Deflector 55 can be actuated by wire 57 to move the distal portion of instrument 63 extending through window 65 in housing 52.

Housing 52 can comprise accommodation space 53 that houses deflector 55. Instrument 63 can comprise forceps, a catheter, or the like that extends through lumen 62. A proximal end of deflector 55 can be attached to housing 62 at pin 61 8 provided to the rigid tip 21. A distal end of deflector 55 can be located below window 65 within housing 62 when deflector 55 is in the lowered, or un-actuated, state. The distal end of deflector 55 can at least partially extend out of window 65 when deflector 55 is raised, or actuated, by wire 57. Instrument 63 can slide on angled ramp surface 51 of deflector 55 to initially deflect the distal end of instrument 63 toward window 65. Angled ramp surface 51 can facilitate extension of the distal portion of instrument 63 extending from window 65 at a first angle relative to the axis of lumen 62. Angled ramp surface 51 can include groove 69, e.g. a v-notch, to receive and guide instrument 63. Deflector 55 can be actuated to bend instrument 63 at a second angle relative to the axis of lumen 62, which is closer to perpendicular that the first angle. When wire 57 is released, deflector 55 can be rotated, e.g., counter-clockwise, back to the lowered position, either by pushing or relaxing of wire 57.

Figure 4A:
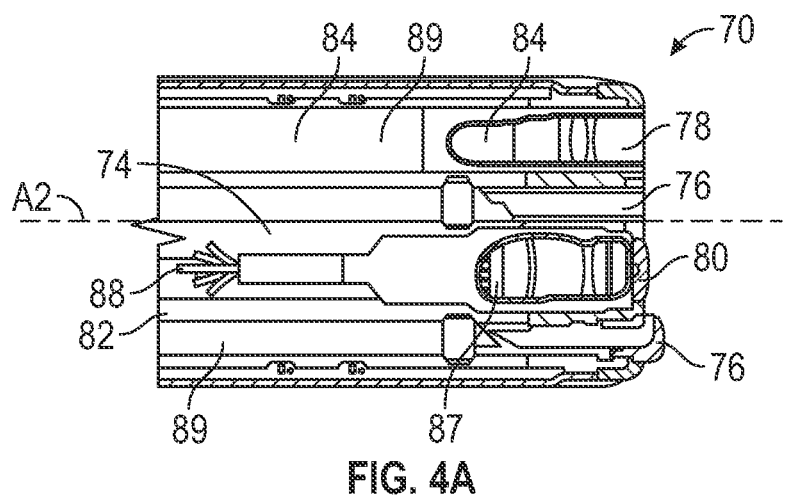
FIG. 4A is an end view of a camera module including optical components for an end-viewing endoscope.
Figure 4B:
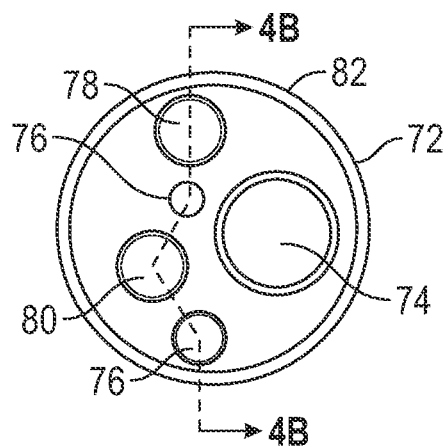
FIG. 4B is a cross-sectional view taken along the plane 4B-4B of FIG. 4A showing the optical components.

FIGS. 4A and 4B illustrate a second example of functional section 30 of endoscope 14 of FIG. 2. FIG. 4A illustrates and end view of functional section 30 and FIG. 4B illustrates a cross-sectional view of functional section 30 taken along section plane 4B-4B of FIG. 4A. FIGS. 4A and 4B each illustrate "end-viewing endoscope" (e.g., gastroscope, colonoscope, cholangioscope, etc.) camera module 70. In end-viewing endoscope camera module 70, illumination and imaging systems are positioned such that the viewing angle of the imaging system corresponds to a target anatomy located adjacent an end of endoscope 14 and in line with central longitudinal axis A2 of endoscope 14.

In the example of FIGS. 4A and 4B, end-viewing endoscope camera module 70 can comprise housing 72, therapy unit 74, fluid outlet 76, illumination lens 78 and objective lens 80. Housing 72 can comprise and endcap for insertion section 28, thereby providing a seal to lumen 82.

As can be seen in FIG. 4B, insertion section 28 can comprise lumen 82 through which various components can be extended to connect functional section 30 with handle section 32 (FIG. 2). For example, illumination lens 78 can be connected to light transmitter 84, which can comprise a fiber optic cable or cable bundle extending to light source 22 (FIG. 1). Likewise, objective lens 80 can be coupled to imaging unit 87, which can be coupled to wiring 88. Also, fluid outlets 76 can be coupled to fluid lines 89, which can comprise a tube extending to fluid source 24 (FIG. 1). Other elongate elements, e.g., tubes, wires, cables, can extend through lumen 82 to connect functional section 30 with components of endoscopy system 10, such as suction pump 26 (FIG. 1) and treatment generator 44 (FIG. 2). For example, therapy unit 74 can comprise a wide-diameter lumen for receiving other treatment components, such as cutting devices and therapeutic devices.

Both side-viewing endoscope camera module 50 of FIGS. 3A and 3B and end-viewing endoscope camera module 70 of FIGS. 4A and 4B have several elements in common. In particular, endoscope camera modules 50 and 70 can include optical components (e.g., objective lenses 60 and 80, prism 66, imaging units 67 and 87, wiring 68 and 88) for collection of image signals, lighting components (e.g., illumination lenses 58 and 78, light transmitters 64 and 84) for transmission or generation of light. Endoscope camera modules 50 and 70 can also include a photosensitive element, such as a charge-coupled device ("CCD" sensor) or a complementary metal-oxide semiconductor ("CMOS") sensor. In either example, imaging units 67 and 87 can be coupled (e.g., via wired or wireless connections) to image processing unit 42 (FIG. 2) to transmit signals from the photosensitive element representing images (e.g., video signals) to image processing unit 42, in turn to be displayed on a display such as output unit 18. In various examples, imaging and control system 12 and imaging units 67 and 87 can be configured to provide outputs at desired resolution (e.g., at least 480p, at least 720p, at least 1080p, at least 4K UHD, etc.) suitable for endoscopy procedures.

As mentioned, the present inventors have recognized that conventional endoscopes, particularly, duodenoscopes, can include elevator sections that comprise elaborate and intricate constructions that can be expensive and difficult to clean. The present inventors have developed solutions to these and other problems by developing endoscopes that can have attachment mechanisms and systems that facilitate simple and easy-to-operate attachment and detachment of camera modules and control modules that can be separated from a disposable insertion section sheath. As such, the camera and control modules can include high-quality or high-performance components that can be reused and enveloped in an easy to clean housing. For example, the cameral module can include a 4K, high-imaging unit that can be contained in a sealed container having cut-outs or windows for imaging and illumination lenses, thereby eliminating or reducing cracks and crevices for biological matter to become lodged. Furthermore, the control module can include a multitude of inputs for fixed or programmable control of functional module outputs, such as buttons or a touchscreen connected to a programmable computer system including, at least, a processor and memory. Furthermore, the control module can be encapsulated for easy cleaning and can wirelessly communicate with the functional module so to be operable from a sterile or non-sterile environment.

Figure 5:
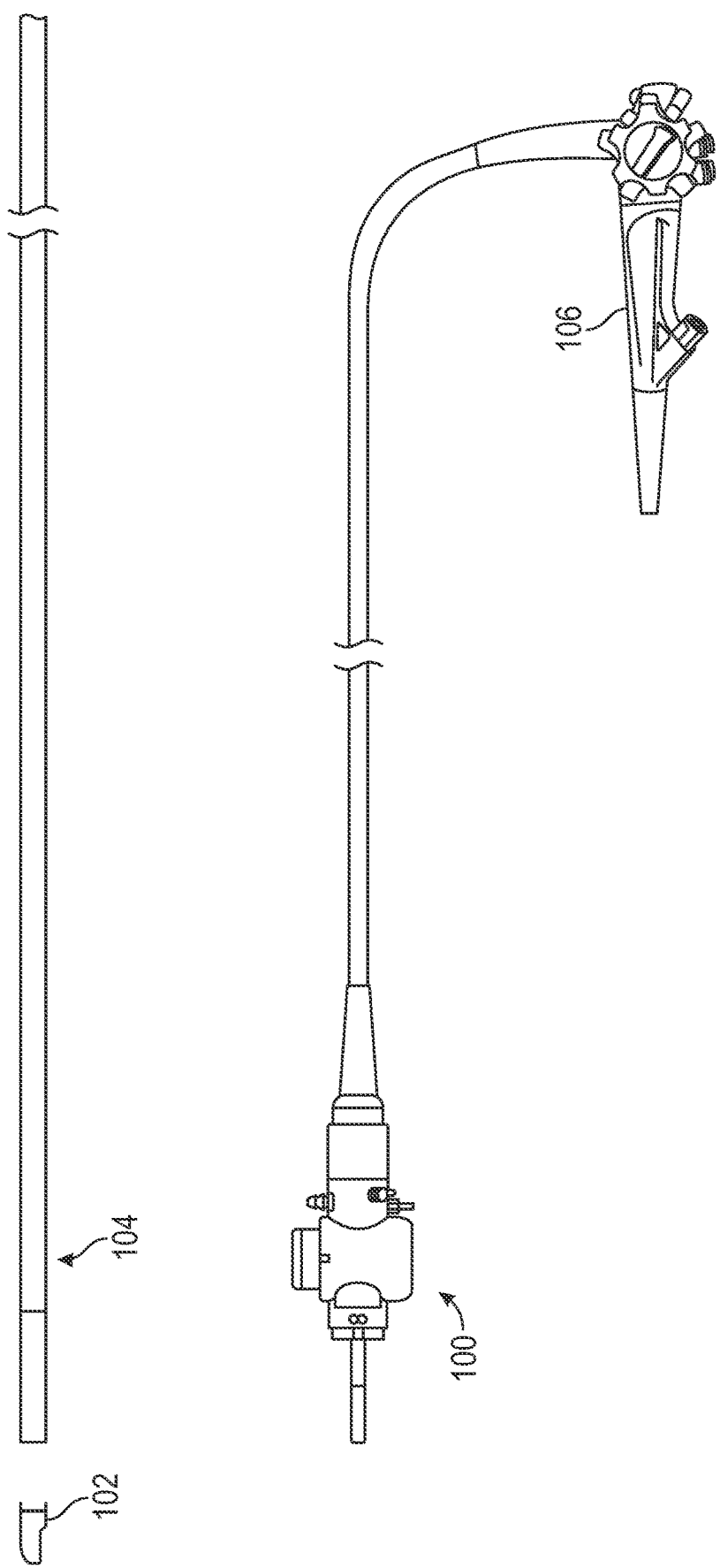
FIG. 5 is a schematic view of a modular endoscope suitable for use as the endoscope of FIGS. 1-4B comprising a camera module, an insertion section module, and a navigation and control module that are configured to be detachable from each other.

FIG. 5 is a schematic view of modular endoscope 100 suitable for use as endoscope 14 and with endoscope camera module 50 of FIGS. 3A and 3B or camera module 70 of FIGS. 4A and 4B. Modular endoscope 100 can comprise a modular detachable functional module 102, insertion section module 104 and navigation and control module 106. Modules 102, 104 and 106 can comprise components including customizable features and components. As such, modular endoscope 100 can be custom-built to perform a specific procedure for a specific patient. Individual modular components can be configured as reusable or disposable components. Therefore, inexpensive or difficult to clean components can be disposed of and expensive or easy to clean components can be reused after appropriate cleaning and sterilizing.

Functional module 102 can comprise functional module 30, camera module 50, camera module 150 (FIG. 6) or other types of modules. Functional module 30 can include one or both of an imaging device, a therapeutic device, and an ancillary therapeutic device, as well as other devices as is described herein.

Insertion section module 104 can comprise a tubular element, sheath or shaft upon and within which functional module 102 can be mounted for insertion into anatomy of a patient.

Figure 13A:
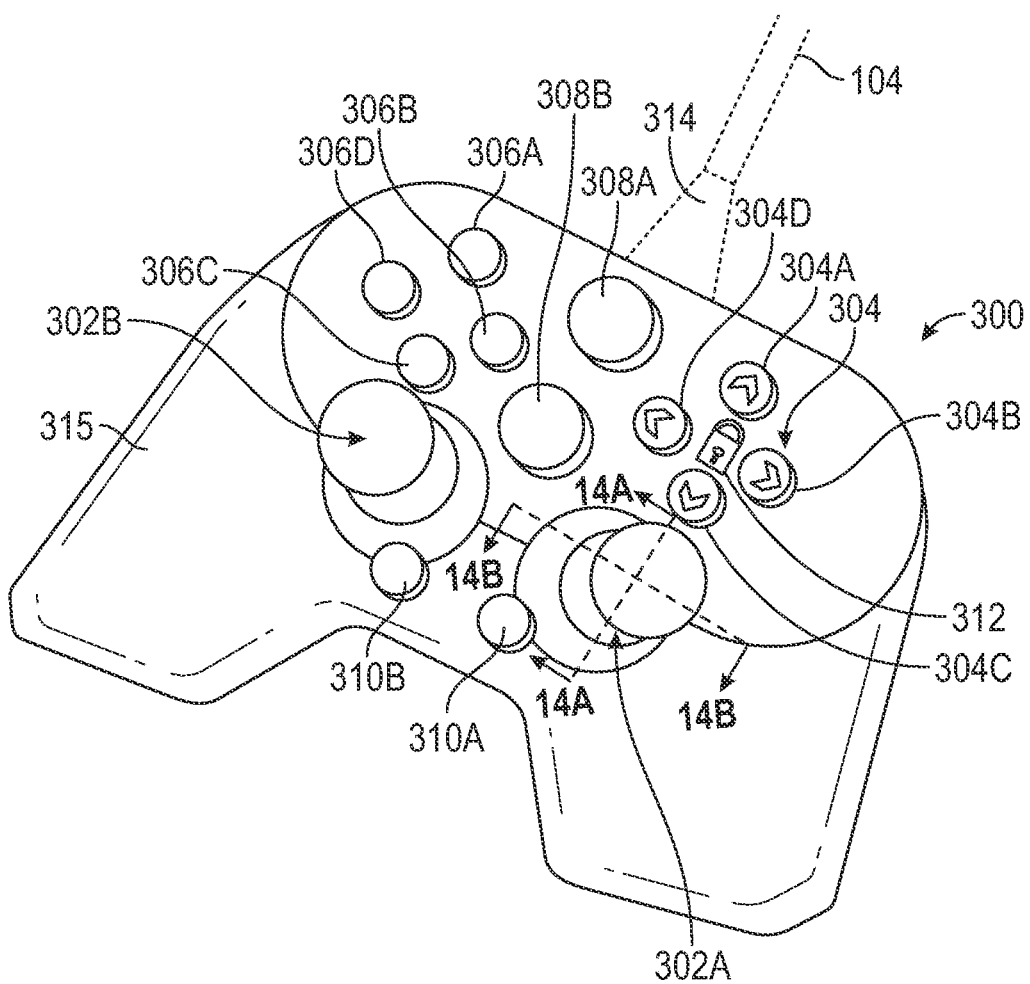
FIG. 13A is a schematic illustration of a navigation and control module for the modular endoscope of FIG. 5 according to a first example.

Navigation and control module 106 can comprise handle section 32, cable section 34 and coupler section 36 of FIGS. 1 and 2, as well as navigation and control module 300 of FIG. 13A and navigation and control module 400 of FIG. 14.

In examples, functional module 102 can comprise camera module 150 as described herein, or the camera modules of the endoscopes described in U.S. provisional patent application 63/024,674 filed on May 14, 2020, titled, "Endoscope with a Low-Profile Distal Section," the entire contents of which is hereby incorporated by reference.

In examples, insertion section module 104 can comprise insertion section 28, which can be configured to include one or more of the sheath and shaft components of U.S. provisional patent application 63/017,901 filed on Apr. 30, 2020, titled, "Insertion Sheath for Modular Endoscope with Detachable and Selectively Disposable Components," the entire contents of which is hereby incorporated by reference.

As mentioned previously, components of endoscope 14 can be modular, as shown by modular endoscope 100 of FIG. 5, such that they can be attached by an operator to initially configure the device for use with a patient, and can be detached by the operator after use with the patient. In other examples, the modular components can be assembled and disassembled by a manufacturer or a decommissioning service without action from the operator. In an example, FIG. 5 illustrates endoscope 14 of FIG. 2, wherein components thereof are shown in a detached state. While FIG. 5 illustrates endoscope 14 as being constructed from three modular components (functional module 102 [functional section 30]), navigation and control module 106 [handle section 32], insertion section module 104 [insertion section 28]), additional or fewer components are contemplated, depending on the surgical procedure to be performed with the configuration of endoscope 14 constructed or designed by the operator. Each of functional module 102, navigation and control module 106, and insertion section module 104 can be detachable from each other. Furthermore, each of modules 102, 104 and 106 can be disposed after a single clinical use. Alternatively, each of modules 102, 104 and 106 can be constructed using materials that would permit several clinical uses. In such cases, modules 102, 104 and 106 can be constructed to withstand sterilization after each clinical use.

In certain advantageous aspects, the modular construction of endoscope 14 of FIG. 2 and modular endoscope 100 of FIG. 5, and as discussed herein, can permit mixing and matching of disposable and reusable modules such that some modules can be reused, such as expensive and/or easy to clean modules, and some modules can be disposable, such as simple and/or difficult to clean modules. For example, certain modules can be detached from the endoscope after a clinical use for sterilization, reprocessing, and reuse for subsequent clinical uses, while the remaining modules can be disposed. For instance, there have been concerns with inadequate reprocessing of portions of duodenoscopes (e.g., elevator portions). As a result, single-use endoscopes that can be disposed after a single clinical use (to prevent infection between uses) have been developed. However, currently available single-use endoscopes, wherein the entire endoscope is disposed of, can be constructed using lower cost materials resulting in a lower price for the endoscope in order to remain competitive per clinical use. In many clinical instances, lower cost materials can lead to poorer clinical performance (e.g., lower quality images, inadequate maneuverability, insertion section module damage during insertion, poorer ergonomic of endoscope handle, etc.). As such, inferior components can result in practitioners preferring not to use such devices.

Accordingly, modular endoscopes 14 and 100 of FIGS. 2 and 5, and others described herein are advantageously constructed such that the end user (e.g., health care providers and facilities) can recover certain modules of endoscope 14 for reuse, while disposing infection prone areas after a single clinical use. In addition, portions of the endoscope that are intended for reuse can be constructed to reduce accumulation of biological materials (such as be being fully encapsulated), and can additionally be fluidly isolated from infection prone areas. Such configurations promote the use of a combination of higher quality (higher cost) reusable components usable over multiple clinical uses, and lower cost, disposable portions, while reducing infection risk, and achieving desired clinical performance. Not only can the disposable components be constructed to include features only needed for the specifically-built procedure, but the materials and construction can be built to only survive one-time use, both of which help reduce the cost of the disposable components. For example, insertion sheaths can be built to survive the stress of only a single operation and does not need to be robustly constructed to survive repetitive stresses of multiple procedures.

In examples, endoscope 100 of FIG. 5 can comprise a duodenoscope, functional module 102 can be configured as a reusable camera module, navigation and the control module 106 can comprise a reusable handle module, and insertion section module 104 can comprise a disposable unit having multiple lumens. Accordingly, the camera module and the navigation and control module can each include connectors that can maintain each of the camera module and the navigation and control module in an attached state to the insertion section module during use with a patient. After each use, the camera module and the navigation and control module can be separated (e.g., using the connectors such as attachment mechanisms 200, 220, 240, 260 and 260 of FIGS. 8A-12B), and reprocessed for subsequent use with a new insertion section module. Conversely, the used insertion section module can be disposed after a single use.

Additionally, the connectors of the camera module and the navigation and the control module as well as the camera module and the navigation and the control module can be constructed of materials and engineered to reduce any ingress of biological materials and can optionally be constructed in a fluid-tight manner.

Modular endoscope 100 can be configured for either a "side-viewing" configuration (as shown in FIGS. 3A-3B) or an "end-viewing" configuration (as shown in FIGS. 4A-4B). In examples, wherein modular endoscope 100 is configured as a side-viewing device (e.g., side-viewing duodenoscope), the distal modular section (e.g., camera module) can be offset from a longitudinal axis of the middle modular section (e.g., insertion module), to accommodate additional components (e.g., elevator mechanisms and the like). In other examples, wherein modular endoscope 100 is configured as an end-viewing device (e.g., gastroscope, colonoscope, cholangioscope, etc.), the distal modular section (e.g., camera module) can be generally co-axially positioned along a longitudinal axis of the middle modular section (e.g., insertion module).

Figure 6A:
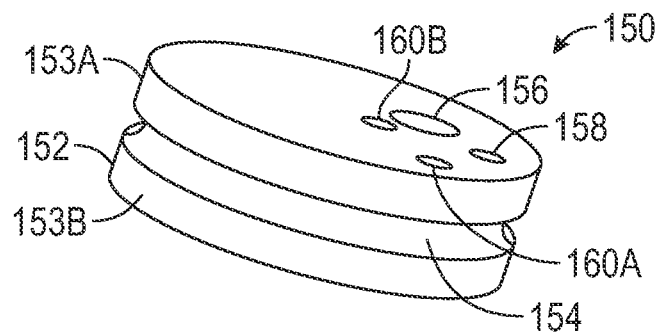
FIG. 6A is a schematic illustration of an example of a camera module of the modular endoscope of FIG. 5.

FIG. 6A is a perspective view of detachable camera module 150 comprising housing 152, groove 154, imaging lens 156, illumination lens 158, an irrigation jets 160A and 160B.

Figure 6B:
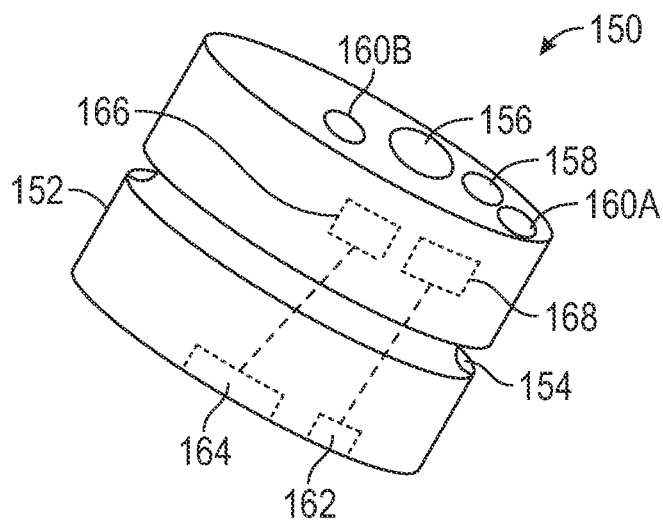
FIG. 6B is schematic illustration of the camera module of FIG. 6A comprising a communication circuit, a rechargeable power source, an imaging unit and an illumination unit.
Figure 7:
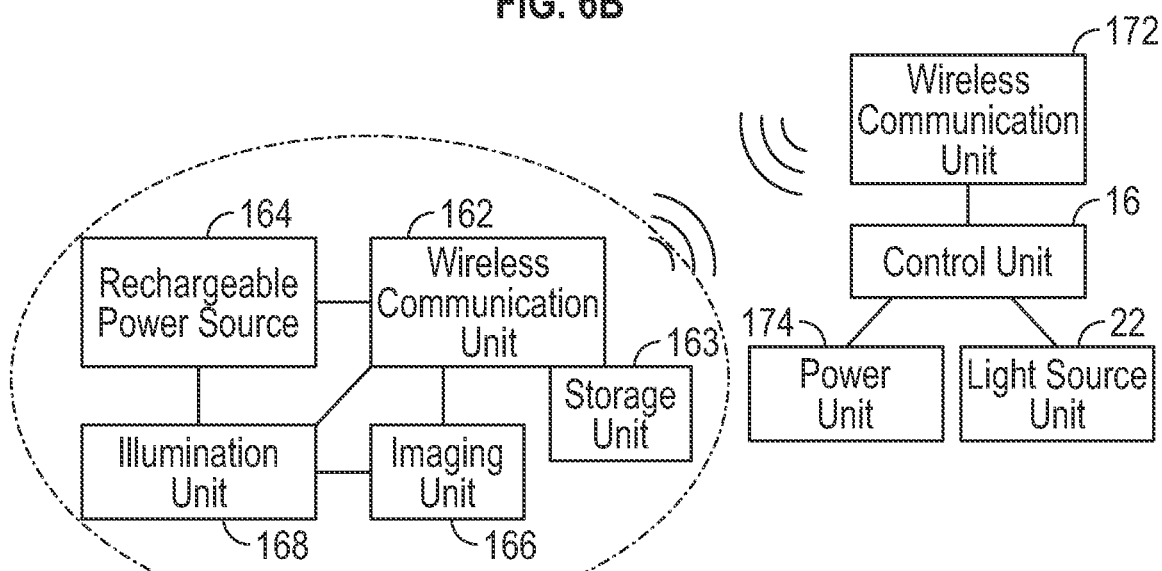
FIG. 7 is a schematic illustration of the modular camera of FIGS. 6A and 6B connected to a wireless imaging and control system according to an example.

FIG. 6B is a schematic view of detachable camera module 150 comprising wireless communication circuit 162, memory 163, rechargeable power source 164, imaging unit 166 and illumination unit 168. FIG. 7 is a schematic illustration of camera module 150 of FIGS. 6A and 6B connected to wireless imaging and control system 12 (FIGS. 1 and 2) according to an example. Wireless imaging and control system 12 can comprise wireless communication unit 172, rechargeable power source 174, image processing unit 42 (FIG. 2) and light source unit 22 (FIG. 2). FIG. 6A-7 are discussed concurrently.

Camera module 150 can be attached to insertion section module 104 of FIG. 5 using any of the attachment mechanisms described herein, such as those shown in FIGS. 8A-12B. FIGS. 6 and 7 illustrate detachable camera module 150 with orifices for irrigation jets 160A and 160B to provide lens cleaning functionalities, etc. However, in other examples, irrigation jets 160A and 160B can be omitted.

Housing 152 can comprise a sturdy, fluid-tight enclosure can be formed to limit accumulation of biofilm or other biological substances during clinical use. In the illustrated examples, camera module 150 can include ports that permit passage of fluids, however, the remainder of housing 152 can be fluid-tight to reduce the chances of fluid ingress or egress, and also can not include seams or other crevices which have a tendency for accumulation of biological substances. In an example, housing 152 can comprise first shell 153A and second shell 153B that can be brought together at groove 154, such as via a snap fit coupling. A seal, such as an O-ring can be positioned in groove 154. Additionally, shells 153A and 153B can be fabricated of a clear or transparent material that can allow light to pass into and out of lenses 156 and 158, thereby avoiding external cracks and crevices where fluid can ingress into housing 152. Alternatively, shell 153A can be provided with ports for lenses 156 and 156 that can be sealed with O-rings. Accordingly, housing 152 of FIGS. 6 and 7 can be detached from insertion section module 104 after each clinical use, and reprocessed before a subsequent clinical use, such as by using the attachment mechanism described with reference to FIGS. 8A-12B.

Camera module 150 can be "self-contained." For instance, detachable camera module 150 can include wireless communication circuit 162, rechargeable power source 164, imaging unit 166 and illumination unit 168 in operative communication with one another, as schematically illustrated in FIG. 7. As such, camera module 150 can be capable of powering itself, capturing images with imaging unit 166, generating light with illumination unit 168, and transmitting captures images to external devices with wireless communication circuit 162 without the aid or intervention of an external device or system.

Rechargeable power source 164 can include one or more batteries (e.g., Lithium ion) that can provide power for the entire duration of clinical procedures (e.g., up to about 8 hours, inclusive). Power source 164 can be "recharged" between use, during sterilization or reprocessing, as explained herein with reference to FIG. 17. Rechargeable power source 164 can be wirelessly recharged through housing 152 or can include a plug or socket into which a power cord or cable, such as power cable 510 (FIG. 17) can be inserted.

Illumination unit 168 can include one or more lamps e.g., LED, as illustrated in FIGS. 6B and 7, or other suitable light sources in a desired spectrum to permit imaging of patient anatomy, for instance according to Olympus Corporation's Narrow Band Imaging or other technologies.

Illumination unit 168 can be coupled to rechargeable power source 164 to provide power to illumination unit 168 for the duration of one or more clinical procedures.

Imaging unit 166 can include one or more of a CCD or CMOS photosensitive element. Imaging unit 166 can be coupled to rechargeable power source 164 to provide power to imaging unit 166 for the duration of one or more clinical procedures. Output of imaging unit 166, e.g., still digital images or digital video, can be conveyed to wireless communication circuit 162 for transmission to devices and systems external to camera module 150.

Wireless communication circuit 162 can establish wireless communication between illumination unit 168, imaging unit 166, rechargeable power source 164, and any of endoscope control unit 16 (as seen in FIGS. 2 and 7). Wireless communication circuit 162 can send and receive wireless signals that can transmit data or instructions between camera module 150 and wireless communication unit 172 of endoscope controller 16. The instructions can include navigational instructions directed toward insertion section module 104 to advance the distal end of endoscope 100 to a desired location within the anatomy. The instructions can also include commands to imaging unit 166 or illumination unit 168, such as turn illumination 168 unit on or off, turn imaging unit 166 on or off, capture image using imaging unit 166, capture video using imaging unit 166 and the like. Wireless communication circuit 162 can further comprise, either integrated into or in communication with, memory 163. Memory 163 can comprise a non-transitory storage medium including information stored therein regarding manufacturing information, model identification information and serial number information related to camera module 150. Furthermore, insertion section module 104 can include a wireless communication circuit and memory that can be configured similarly to wireless communication circuit 162 and memory 163 to transmit and store information relating to the manufacturing, model and serial number information of a particular insertion section module. 104. Memory 163 can comprise a tangible computer-readable media such as hard disks, removable magnetic disks, removable optical disks (e.g., compact disks and digital video disks), magnetic cassettes, memory cards or sticks, random access memories (RAMs), read only memories (ROMs), and the like.

In advantageous examples, the wireless signals can include data (e.g., scope identification such as serial number), camera module location in the anatomy (e.g., using Olympus Corporation's ScopeGuide technology), battery power remaining, strength of wireless signal, and images or video recorded by the imaging unit, and the like.

According to illustrative examples, wireless communication circuit 162 can include transponders or beacons that can communicate using well-established wireless communication protocols, such as 3G, 4G, 5G, Bluetooth®, and wireless internet protocols such as 802.11 and WiFi. In advantageous aspects, Bluetooth can be used to achieve desirable data transfer rates and low power consumption rates.

Additionally, wireless communication circuit 162 can also include near-field communication (NFC or radiofrequency) chips or devices to communicate with other modules (e.g., an NFC chip provided on a insertion section module having memory) to validate identification data (e.g. serial number of the insertion section module) stored in the memory. Wireless communication circuit 162 can transmit the identification data collected from insertion section module 104 to control unit 16 and verify that insertion section module 104 is appropriate (e.g., compatible with camera module 150) and ready for use. In addition, such examples can ensure that a correct insertion section module 104 has been used for a particular clinical procedure. In such cases, control unit 16 can be programmed (e.g., using computer readable instructions) to:

receive identification data of the insertion section module read by the near-field communication chip of the camera module;
verify that the insertion section module is appropriate;
optionally, displaying specifications (size, manufacturer, serial number, prior use data etc.) of the insertion section module for a health care provider, such as on display unit 18;
optionally, displaying a message on display unit 18 that the device is ready for use if the specification data of the insertion section module matches one or more criteria (not previously used, correct size, type, manufacturer, valid serial number) for a clinical procedure; and
displaying a message on display unit 18 the device is not ready for use if the specification of the working section does not match one or more criteria (incorrect type, manufacture or size of scope, prior use, serial number is not authorized).

According to advantageous aspects, in examples where an NFC chip is used, the above steps can be performed before the insertion and coupling of camera module 150 to insertion section module 104. For example, wireless communication circuit 162 of camera module 150 can interrogate a wireless communication circuit of insertion section module 104 and the wireless communication circuit of insertion section module 104 can communicate with control unit 16 of imaging and control system 12 to, for example, ensure that only compatible insertion section modules 104 are used with camera module 150 and are suitable for the intended medical procedure.

In addition, or in the alternative, in certain examples, camera module 150 can be constructed as being similar to the Olympus Corporation's Endocapsule endoscopy system.

FIGS. 8-12 illustrate various attachment mechanisms for attaching detachable camera module 150, as well as any of the other examples disclosed or referenced herein, to insertion section module 104, as well as any of the other examples disclosed or referenced herein. In various examples, the disclosed attachment mechanisms can attach to camera module 150 via groove 154 or another attachment feature, such as a hole, socket, channel and the like.

The attachment mechanisms of FIGS. 8A-12B can each be configured to withstand loads experienced during insertion of scope 100 inside a patient anatomy. Furthermore, in examples where camera module 150 is intended to be reusable, portions of groove 154 on camera module 150 can be engineered to withstand mechanical loads, high pressure and temperature water washing, UV radiation and the like.

Figure 8A:
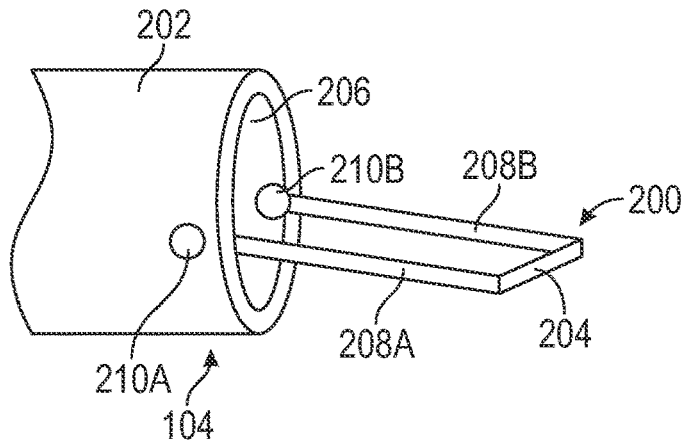
FIG. 8A is a schematic illustration of a first example of an attachment mechanism for securing detachable camera modules of the present disclosure to a distal portion of the insertion section module of the modular endoscope of FIG. 5, the attachment mechanism comprising a retention band.
Figure 8B:
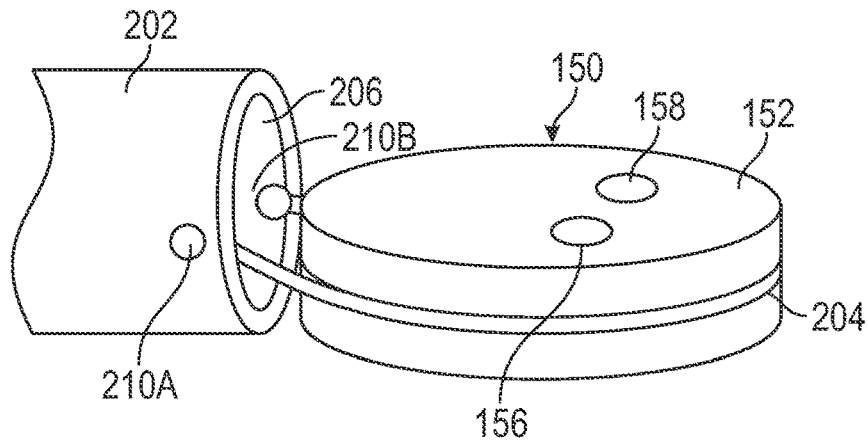
FIG. 8B is a schematic illustration of the camera module of FIG. 6 secured with the attachment mechanism of FIG. 8A.

FIG. 8A is a schematic illustration of attachment mechanism 200 for securing detachable camera module 150 of the present disclosure to distal portion 202 of elongate insertion section module 104 (FIG. 5) of modular endoscope 100 of FIG. 5. FIG. 8B is a schematic illustration of camera module 150 of FIG. 6 secured with retention band 204 of FIG. 8A. In the example of FIGS. 8A and 8B, attachment mechanism 200 can comprise retention band 204. FIGS. 8A and 8B are discussed concurrently.

Distal portion 202 of insertion section module 104 can comprise a tubular body defining lumen 206. Retention band 204 can comprise a loop, r partial loop, having first end 208A connected to distal portion 202 at attachment 210A and second end 208B connected to distal portion 202 at attachment 210B.

Retention band 204 can comprise a rigid or elastic member extending between first end 208A and second end 208B. Attachments 210A and 210B can comprise fixed or releasable connections between retention band 204 and distal portion 202. In examples, attachments 210A and 210B can comprise metallurgical bonds (e.g., welds or solders), chemical bonds (e.g., adhesives or glues) or mechanical bonds (e.g., fasteners and pins).

In an example, retention band 204 can comprise an elastic band and attachments 210A and 210B can be fixed. As such, as shown in FIG. 8B, camera module 150 can be slipped into retention band 204 with retention band 204 expanded, e.g. by a user. Retention band 204 can be released to be positioned within groove 154. As such, in a relaxed state, retention band 204 can be smaller than the diameter of housing 152, but can be expanded to be larger than the diameter of housing 152. Retention band 204 can additionally be smaller than the diameter of groove 154 in a relaxed state such that retention band 204 can apply tension to housing 152.

In another example, retention band 204 can comprise a rigid band and one or both of attachments 210A and 210B can comprise releasable connections. In particular, one or each of attachments 210A and 210B can comprise a clasp, such as the one described with reference to FIG. 8C. As such, retention band 204 can extend between first end 208A and second end 208B to have a radius smaller than housing 152 and just greater than the radius of groove 154. Thus, when both of attachments 210A and 210B are closed or clasped, retention band 204 can be trapped within groove 154 such that housing 152 cannot be released from retention band 204. In examples, the clasps comprising attachments 210A and 210B can be spring-loaded. Thus, attachment mechanism 200 can be actuated by pressing open a spring-loaded clasp, to dislodge an indent at the distal edge. The dislodged indent can allow arms of the clasp to spread laterally allowing placement of camera module 150. Once camera module 150 is placed, the arms can be closed, and the indent reinstated.

Figure 8C:
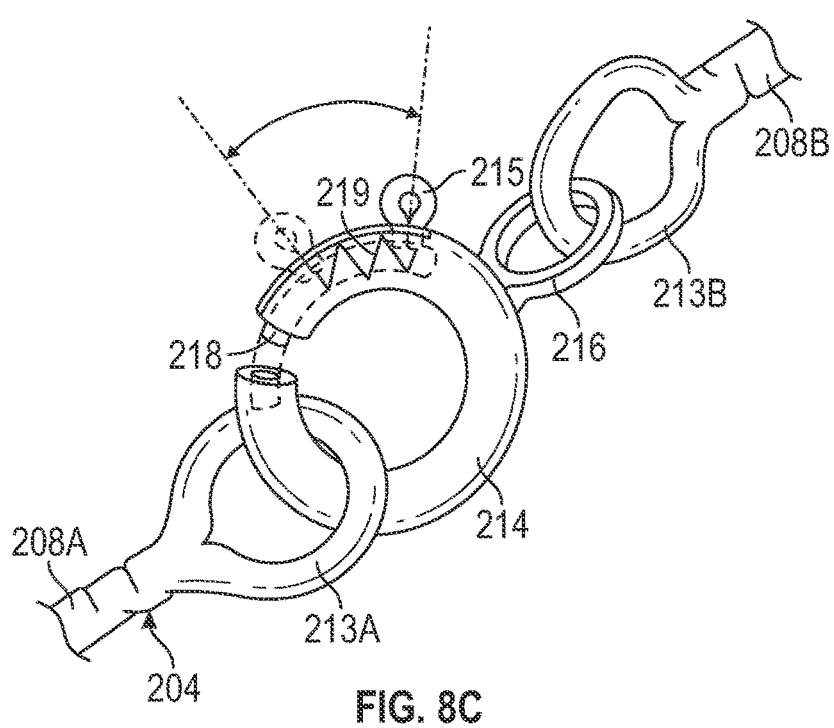
FIG. 8C is a perspective view of a clasp mechanism suitable for use with the retention band of FIGS. 8A and 8B.

FIG. 8C is a perspective view of clasp mechanism 212 suitable for use with retention band 204 of FIGS. 8A and 8B. Clasp mechanism 212 can comprise eyelets 213A and 213B, hook 214, handle 215, ring 216, latch 218 and spring 219. Ring 216 can be attached to second end 208B of retention band 204. Hook 214 can be releasably attached to first end 208A of retention band 204. Handle 215 can be actuated to move latch 218 toward ring 216 (to the right with reference to FIG. 8C) to open hook 214. As such eyelet 213A can be positioned inside hook 214. Handle 215 can be released to close hook 214. Force from spring 219 can push latch 218 back into engagement with hook 214 to close hook 214.

Figure 9A:
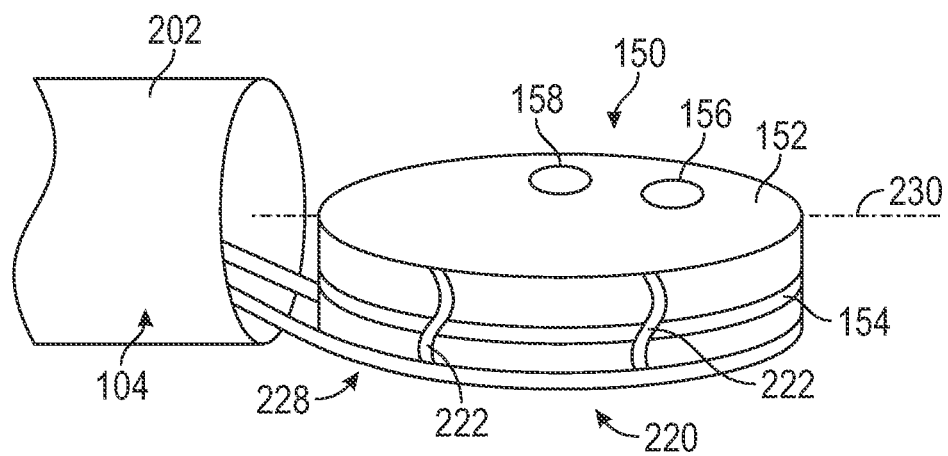
FIG. 9A is a schematic illustration of a second example of an attachment mechanism for securing detachable camera modules of the present disclosure to a distal portion of the insertion section module of the modular endoscope of FIG. 5, the attachment mechanism comprising a retention clip system.
Figure 9B:
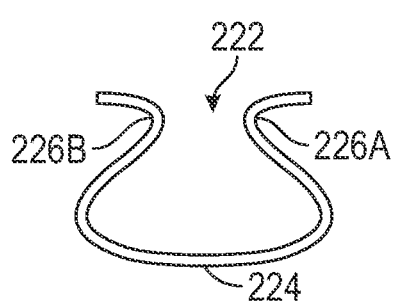
FIG. 9B is a schematic illustration of a clip for the retention clip system of FIG. 9A.
Figure 9C:
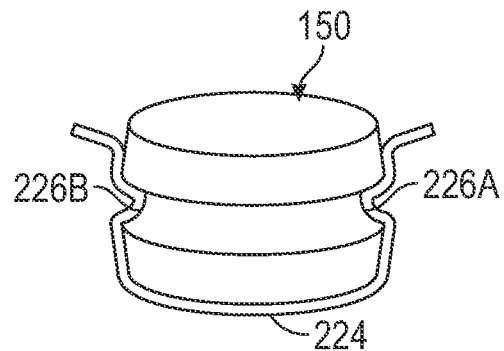
FIG. 9C is a schematic illustration of the camera module of FIG. 6 secured with the attachment mechanism of FIG. 9A.
Figure 9D:
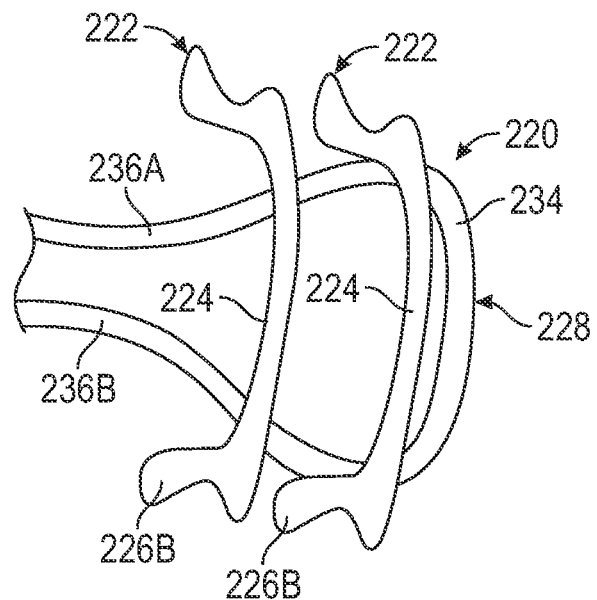
FIG. 9D is a schematic illustration of the retention clip system of FIG. 9A showing retention clips mounted to a platform.

FIG. 9A is a schematic illustration of attachment mechanism 220 for securing detachable camera module 150 of the present disclosure to distal portion 202 of elongate insertion section module 104 of modular endoscope 100 of FIG. 5. FIG. 9B is a schematic illustration of attachment mechanism 220 comprising retention clip 222. FIG. 9C is a schematic illustration of camera module 150 of FIG. 6 secured with attachment mechanism 220 of FIG. 9A. FIG. 9D is a schematic illustration of attachment mechanism 220 of FIG. 9A showing retention clips 222 mounted to platform 228. FIGS. 9A-9D are discussed concurrently.

Retention clip 222 can comprise a spring bracket comprising base 224 and first and second ends 226A and 226B. Attachment mechanism 220 can comprise one or more retention clips 222 mounted to platform 228. Platform 228 can comprise a flange or hoop coupled to distal portion 202 upon which retention clips 222 can be mounted. Platform 228 can be attached to distal portion 202 by any suitable means, including via the use of fasteners, metallurgical bonding methods, glues and adhesives. Bases 224 of retention clips 222 can be secured to platform 228 such that ends 226A and 226B extend radially inward toward centerline 230. First and second ends 226A and 226B can be contoured to match the shape of housing 152 including groove 154. Retention clips 22 can be actuated (e.g., by manual force during attachment of camera module 150) onto groove 154 in housing 152 of camera module 150 (as illustrated in FIG. 6). As such, housing 152 of camera module 150 can be pushed down radially in between ends 226A and 226B such that ends 232A and 232B penetrate into groove 154.

As can be seen in FIG. 9D, platform 228 can comprise base 234. In the illustrated examples, base 234 can comprise a hoop having ends 236A and 236B that can be coupled to distal portion 202 by any suitable means, such as those described herein. As such, bases 224 of retention clips 222 can be seated in the hoop of base 234 with ends 226A and 226B projecting outward from platform 228 to receive housing 152. Bases 224 can be coupled to base 234 via metallurgical, chemical or mechanical fastening means.

Figure 10A:
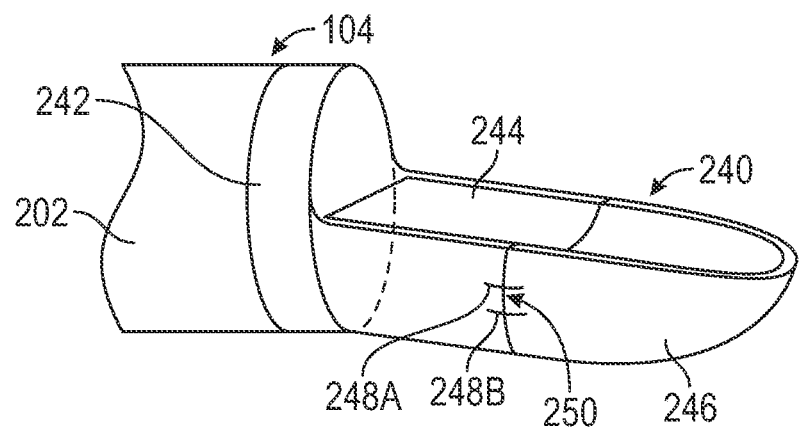
FIG. 10A is a schematic illustration of a third example of an attachment mechanism for securing detachable camera modules of the present disclosure to a distal portion of the insertion section module of the modular endoscope of FIG. 5, the attachment mechanism comprising a hinged basket.
Figure 10B:
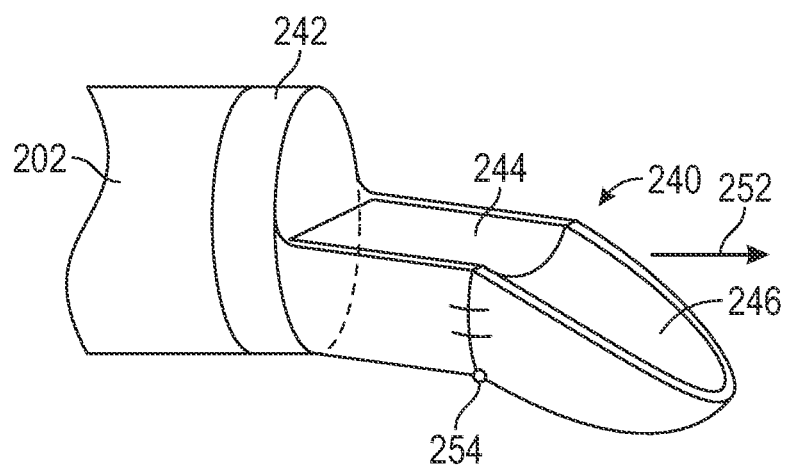
FIG. 10B is a schematic illustration of the hinged basket of FIG. 10A in an expanded state.

FIG. 10A is a schematic illustration of attachment mechanism 240 for securing detachable camera module 150 of the present disclosure to distal portion 202 of elongate insertion section module 104 of modular endoscope 100 of FIG. 5. FIG. 10B is a schematic illustration of attachment mechanism 240 of FIG. 10A in an expanded state. FIGS. 10A and 10B are discussed concurrently.

Attachment mechanism 240 can comprise a hinged mechanism including base 242, fixed jaw 244 and movable jaw 246. Fixed jaw 244 can be rigidly secured to base 242. Fixed jaw 244 and moveable jaw 246 can be coupled by one or more devices acting as hinges and springs, such as hinges 248A and 248B at joint 250. In the illustrated example, hinges 248A and 248B can comprise elastic bands. Hinges 248A and 248B are shown in one side of jaws 244 and 246 and an analogous pair can be disposed on the opposed side of jaws 244 and 246. Fixed jaw 244 and moveable jaw 246 can comprise a holder or housing for receiving camera module 150 and, as such, can comprise an internal volume that conforms or substantially conforms to the outer shape of housing 152 of camera module 150. Hinges 248A and 248B can have opposite ends connected to fixed jaw 244 and moveable jaw 246, respectfully. Hinges 248A and 248B can comprise both spring properties and hinge properties. For example, hinges 248A and 248B can comprise elastic bands that can be stretched to position moveable jaw 246 in the extended or expanded position of FIG. 10B. In other examples, moveable jaw 246 can be connected to fixed jaw 244 via separate spring mechanisms that pull moveable jaw 246 into engagement with fixed jaw 244 as shown in FIG. 10A and hinge mechanisms that allow moveable jaw 246 to be pivoted relative to fixed jaw 244 at a fixed pivot axis, such as pinned axis 254 When moveable jaw 246 is pulled away from fixed jaw 244, e.g., in distal direction 252, or rotated at axis 254, moveable jaw 246 can be disrupted at joint 250 to expand the internal volume of the holder formed by fixed jaw 244 and moveable jaw 246. As a result, housing 152 of camera module 150 can be positioned between fixed jaw 244 and moveable jaw 246 within the internal volume. When moveable jaw 246 is released and returned to the closed position of FIG. 10, housing 152 can become fixed within the internal volume between fixed jaw 244 and moveable jaw 246.

Figure 11A:
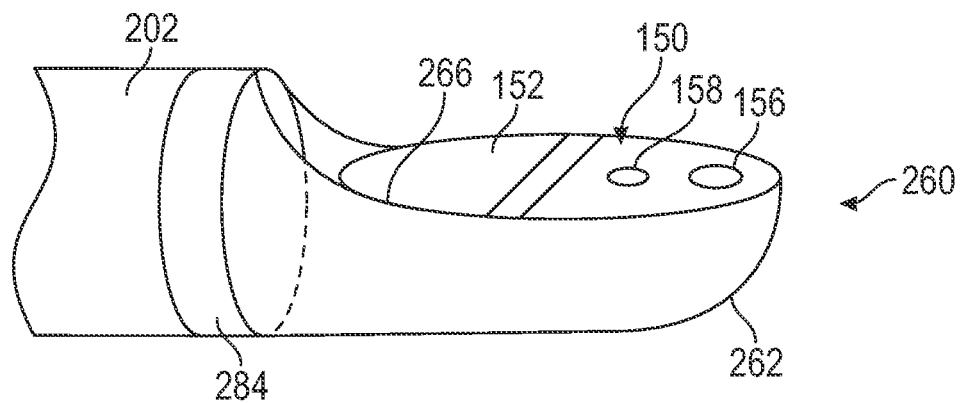
FIG. 11A is a schematic illustration of a fourth example of an attachment mechanism for securing detachable camera modules of the present disclosure to a distal portion of the insertion section module of the modular endoscope of FIG. 5, the attachment mechanism comprising an expandable sleeve.

FIG. 11A is a schematic illustration of attachment mechanism 260 for securing detachable camera module 150 of the present disclosure to distal portion 202 of elongate insertion section module 104 of modular endoscope 100 of FIG. 5. Attachment mechanism 260 can comprise expandable sleeve 262. Sleeve 262 can comprise base 264, opening 266 and interior space 268. Sleeve 262 can comprise a boot or bag configured to partially envelope housing 152 of camera module 150. Sleeve 262 can be attached to base 264 that can attach to distal portion 202. Sleeve 262 can be fabricated from a resilient material that can be stretched or expanded to allow housing 152 of camera module 150 to pass through opening 266. As can be seen in FIG. 11A, sleeve 262 can include an adjustable or stretchable strap that can extend across opening 266 to help secure camera module 150 within sleeve 262.

Figure 11B:
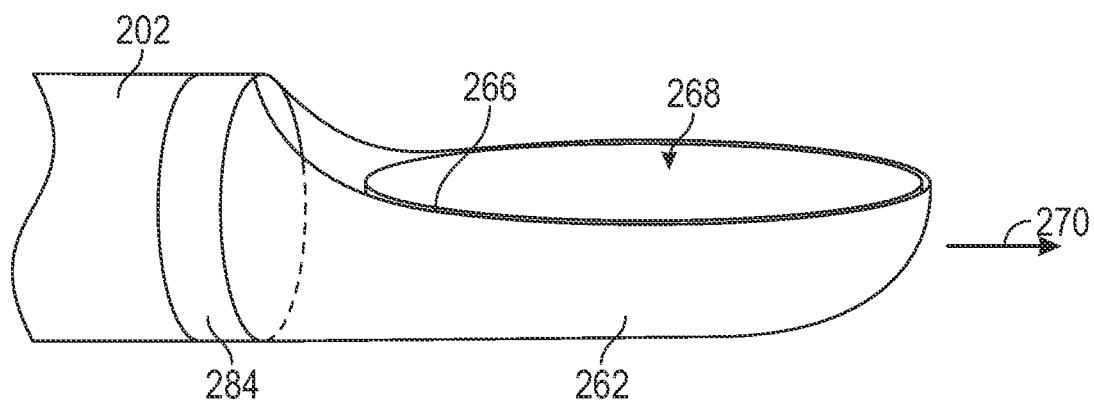
FIG. 11B is a schematic illustration of the expandable sleeve of FIG. 11A in an expanded state.

As can be seen in FIG. 11B, expandable sleeve 262 can be stretched in distal direction 270 to expand opening 166 to at least one dimension being greater than the diameter or width of housing 152. As such, housing 152 can be pushed through opening 266 and into the interior space 268. Once housing 152 is within interior space 258, sleeve 262 can contract or retract to a smaller size to envelop and at least partially conform to the shape of housing 152.

FIG. 12A is a schematic illustration of attachment mechanism 280 for securing detachable camera module 150 of the present disclosure to distal portion 202 of elongate insertion section module 104 of modular endoscope 100 of FIG. 5. Attachment mechanism 280 can comprise threaded engagement 282. Threaded engagement 282 can comprise threaded socket 284 for connecting to attachment mechanism 280 and threaded rim 286 connected to, or part of, distal portion 202. FIG. 12B is a schematic illustration of attachment mechanism 280 with threaded socket 284 separated from threaded rim 286.

Attachment mechanism 280 can comprise any of the attachment mechanisms disclosed or contemplated herein, such as attachment mechanisms 200, 220, 240 and 260. In the illustrated examples, threaded socket 284 can comprise a circular ring into which distal portion 202 can be inserted via threaded engagement. As such threaded socket 284 can comprise internal threading 288 (shown in phantom in FIG. 12B) and threaded rim 286 can comprise a portion of distal portion 202 having external threading 290. In other examples distal portion 202 can be provided with internal threading to engage external threading of socket 284.

In examples where endoscope 100 is a duodenoscope, distal portion 202 of insertion section module 104 can be provided with an elevator portion (e.g., elevator 54 of FIG. 3A) for orienting and supporting a plurality of therapeutic tools (e.g., biopsy forceps, cholangioscope, and the like). In such configurations, attachment mechanisms 200, 220, 240 and 260 of any of FIGS. 8A-12B can be located adjacent, e.g., radially outward of central axis CA if insertion section module 104, to the elevator mechanism. In other configurations, the attachment mechanism can be position axially spaced from the elevator mechanism, as is shown in FIG. 12B with camera module 150 being axially (distally) displaced from elevator 54.

Housing 152 of camera module 150 can be positioned in the various attachment mechanisms disclosed herein in different orientations relative to central axis CA, as can be seen in FIGS. 8B, 9A, 11A and 12B. Furthermore, though the described attachment mechanisms are shown in side-viewing configurations, the attachment mechanisms can be configured in end-viewing configurations. As shown in FIG. 12B, housing 152 of camera module 150 and attachment mechanism 280 can be have other shapes besides the round or circular shaped described herein.

In optional examples, a protective sheath can be placed around camera module 150 to further reduce ingress of biological substances into the camera module. The protective sheath can comprise a flexible bag that can be positioned over camera module 150 and attachment mechanism 280 and secured to distal portion 202. In examples, the protective sheath can be secured by threaded engagement 282. In other examples, the protective sheath can comprise a hard-sided structure matching the shape of attachment mechanism 280 that is secured by force for or snap fit at threaded socket 284.

In examples, attachment mechanism 280, as well as the other attachment mechanisms disclosed herein, can include fluid outlets 76 that can connect to fluid lines 89 via conduits 292 (only one within attachment mechanism. Additionally, distal section 202 can comprise lumen 82 through which other components or capabilities can be inserted to connect to attachment mechanism 280. In other examples, distal section 202 can be sealed off, such as for use with fully independently functional camera modules.

According to some examples, navigation and control module 106 (FIG. 5) of modular endoscope 100 can include ergonomically shaped handle 32 with controls, such as buttons and knob 38, that can permit well-known endoscope navigation and control functionalities. While handle 38 can include any of the handles known in the art (e.g., handles available with Olympus Corporation's endoscopes, such as TJF-Q180V or TJF-Q190V series endoscopes), in the alternative, the present disclosure provides detachable navigation and control modules according to one or more examples.

Figure 14A:
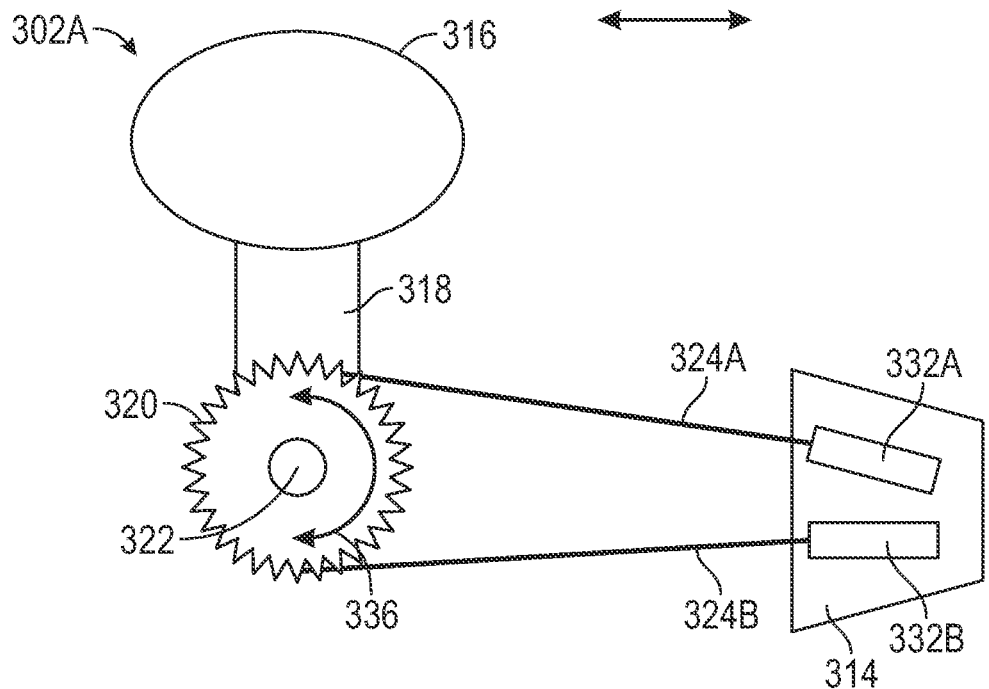
FIG. 14A is a schematic illustration of a sectional view of the navigation and control module of FIG. 13A taken along the plane 14A-14A.
Figure 14B:
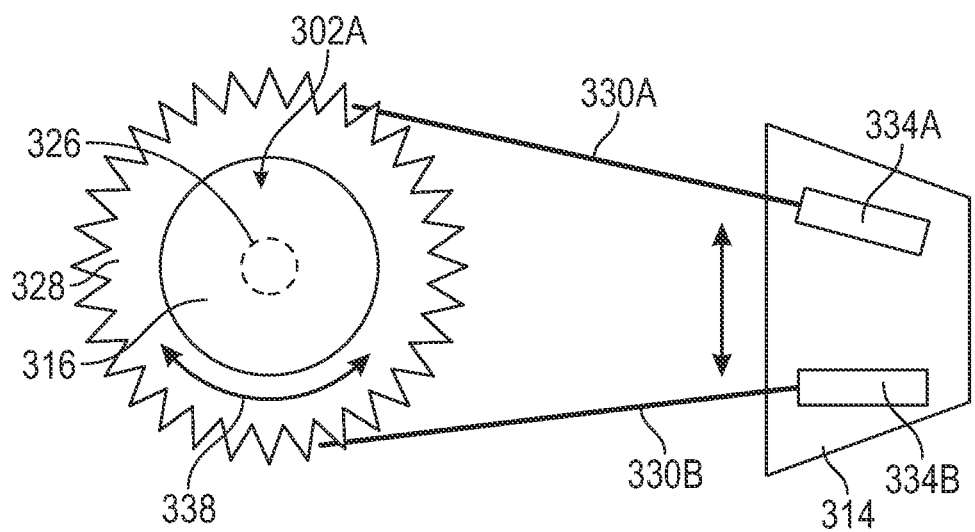
FIG. 14B is a schematic illustration of a sectional view of the navigation and control module of FIG. 13A taken along the plane 14B-14B.

FIGS. 13A, 14A and 14B schematically illustrate detachable navigation and control module 300 comprising an example of navigation and control module 106 according to the present disclosure. As shown in FIG. 14, navigation and control module 106 can include joysticks 302A and 302B, arrow buttons 304A-304D, auxiliary buttons 306A-306D, programmable buttons 308A and 308B, lock buttons 310A and 310B, lock indicator 312 and coupler 314.

Navigation and control module 300 can be detachably coupled to insertion section module 104, such as via coupler 314. In addition, navigation and control module 300 can be fluidly isolated from insertion section module 104, and can therefore be in a sterile environment for reuse after using in a single clinical procedure. For examples, holes in housing 315 for each of the illustrated joysticks and buttons can be sealed with an O-ring or the like. In additional examples, the illustrated buttons can comprise portions of housing 315 connected thereto by monolithic membranes in housing 315. Housing 315 can be ergonomically shaped to allow a user to grip module 300 and easily manipulate joysticks 302A and 302B and buttons 304A-310B. Although module 300 is illustrated as having joysticks and buttons, module 300 can be configured to include other operator inputs, such as triggers and gesture controllers (e.g., gyroscopes).

As shown in FIGS. 14A and 14B, joystick 302A can include joystick driver 316, pivot shaft 318, pivot gear 320, up/down axis 322, angulation wires 324A and 324B, rotation shaft 326, rotation gear 328 and pull wires 330A and 330B.

Joystick 302A can be configured to control the directionality of insertion section module 104, such as by acting upon pull wires. Joystick 302A can replace the up-down and right-left angulation knobs (e.g., knob 38 of FIG. 2) available on conventional endoscope handles.

Joystick driver 316 can be moved in up-down and right-left directions by a user, such as by engagement with a thumb, to advance distal end 202 of insertion section module 104. While a single joystick driver can be sufficient, in certain advantageous examples, a second joystick driver, provided by joystick 302B in examples, can be included in navigation and control module 300. Joystick 302B can advantageously drive a second endoscope. For instance, in certain duodenoscopy procedures (e.g., Endoscopic Retrograde Cholangio-Pancreatography, hereinafter "ERCP" procedures) an auxiliary scope (also referred to as daughter scope, or cholangioscope) can be attached and advanced through the working channel, (e.g., within insertion section module 104) of the "main scope" (also referred to as mother scope or duodenoscope). In such instances, it can be advantageous to include joystick 302B for navigating (e.g., advancing, up-down or right-left angulating) the auxiliary scope.

With continued reference to FIG. 13A, navigation and control module 300 can include one or more buttons. For example, in examples, module 300 can include buttons 310A and 310B for locking the angulation provided by joystick 302A. Buttons 310A and 310B can function similarly to (and interface similarly with) angulation buttons of endoscope handle shown in FIG. 2. Button 310A can comprise an "up" lock button that prevents joystick 302A from moving up. Button 310B can comprise a "right" lock button that prevents joystick 302A from moving right. Button 310C can comprise an "down" lock button that prevents joystick 302A from moving down. Button 310D can comprise a "left" lock button that prevents joystick 302A from moving left. Buttons 310A-310D can be configured to physically obstruct movement of joystick 302A, via appropriate linkages and the like, or can be configured to electronically actuate, e.g., via motor, a linkage to obstruct movement of joystick 302A.

Module 300 can also include additional buttons for facilitating other endoscope functionalities, including programmable functionalities (e.g., capture image, record video, open suction valve, open irrigation valve, close suction valve, close irrigation valve, and the like). Button 308A can be configured to command camera module 150 to operate imaging unit 166. Button 308B can be configured to command camera module 150 to operate illumination unit 168. Furthermore, buttons 308A-308D can be programmable, or can provide angulation locks for the auxiliary scope, similar to the buttons 304A-304D. Additional buttons can be provided to improve ergonomic comfort for the operator e.g., quick lock buttons positioned near the joystick driver to easily lock the scope in the current location without requiring the operator to remove their fingers from the joystick driver, or additional buttons for elevator functionality in duodenoscopes.

FIG. 14A shows a section view through joystick 302A, according to an example, taken along plane 14A-14A shown in FIG. 13A. FIG. 14B shows a section view through joystick 302A, according to an example, taken along plane 14B-14B shown in FIG. 13A. Navigation and control module 300 can be operatively coupled to insertion section module 104 to enable angulation and/or other controls. For example, according to an example, joystick driver 316 can be connected via gear 320 to angulation wires 324A and 324B and gear 328 to angulation wires 330A and 330B. (or suitable tension adjusting mechanisms) provided on the working module section (e.g., at the bending section) to control angulation (up-down, right-left). Coupler 314 can include sockets 332A and 332B that can couple angulation wires 324A and 324B to wires within insertion section module 104. Coupler 314 can also include sockets 334A and 334B that can couple angulation wires 330A and 330B to wires within insertion section module 104.

As shown in FIG. 14A, as an operator manipulates joystick driver 316 in a back and forth motion as shown by arrow 336, the operation motion is transmitted through shaft 318 to gear 320 on axis 322. Gear 320 can be coupled to angulation wires 324A and 324B to control angulation of endoscope 100, such as in up and down directions. Likewise, as shown in FIG. 14B, as an operator manipulates joystick drive 316 in a rotational motion as shown by arrow 338, the operation motion is transmitted through shaft 318 to gear 328 on axis 326. Gear 328 can be coupled to angulation wires 330A and 330B to control angulation of endoscope 100, such as in left and right directions. Though not illustrated for simplicity, gears 322 and 328 can be connected to gearing systems that can amplify or dampen the movements of joystick 302A to produce greater or less correlation in the movement of joystick 302A with the movement of angulation wires 324A, 324B, 330A and 330B.

While FIGS. 14A and 14B illustrate the angulation mechanism associated with the main scope (e.g., of insertion section module 104), joystick 302B (FIG. 13A) cab similarly be coupled to angulation wires of an auxiliary scope (e.g., daughter scope or cholangioscope) to control angulation thereof for certain procedures (e.g., ERCP procedures). In yet another configuration, one of joysticks 302A and 302B can be configured to control up-down angulation of the main scope, while the other of joysticks 302 and 302B can be configured to control left-right angulation.

Figure 13B:
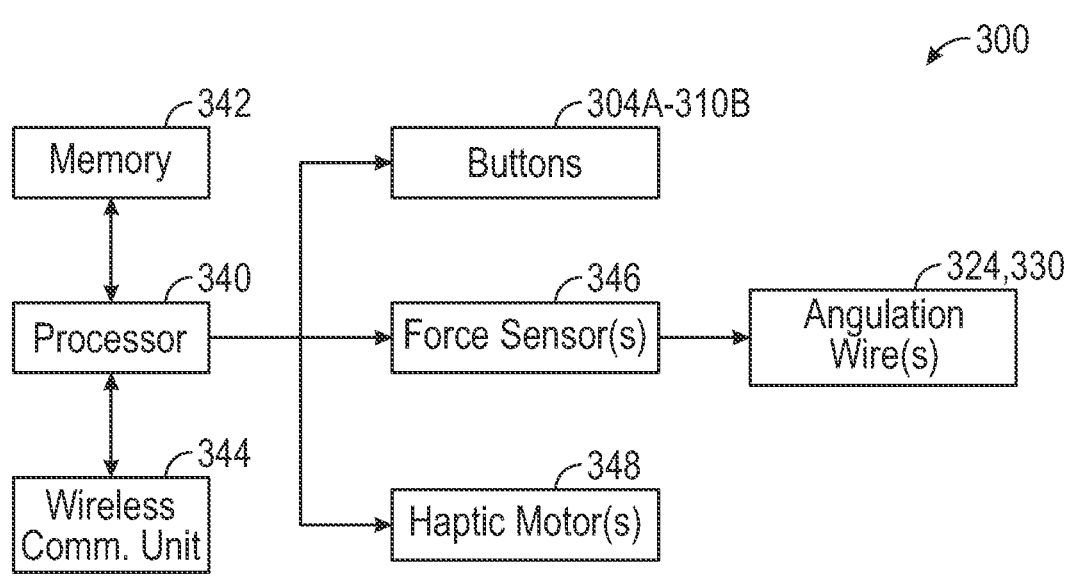
FIG. 13B is a schematic illustration of a control circuit for the navigation and control module of FIG. 13A.

FIG. 13B is a schematic illustration of a control circuit for navigation and control module 300 of FIG. 13A. Controller 300 illustrated in FIGS. 13A-14B can, in certain optional examples, include appropriate electronics for communicating with and controlling other components, such as camera module 150. The control circuit can include processor 340, memory 342, wireless communication unit 344, force sensors 346 and haptic motors 348. Furthermore, the control circuit can be connected to a power source, such as a wirelessly rechargeable battery. For example, wireless communication unit 344 can comprise a wireless transponder, beacon, or other circuitry to wirelessly communicate with camera module 150 and/or insertion section module 104 according to any of the disclosed examples. In addition, controller 300 illustrated in FIGS. 13A-14 can be programmed to provide haptic feedback (e.g., by vibration of the joystick) to alert the user of too much pushing or bending force or other adverse outcomes during insertion. For example, controller 300 be operatively coupled to one or more sensors 346 (e.g., force transducer or proximity sensor) to detect force or contact. Processor 340 and memory 342 can comprise a controller that can be programmable to: receive sensor input from sensors 346, determine if sensor input exceeds thresholds (force exceeds a safe limit, proximity to an abdominal wall is below a safe limit) and provide a signal to an electromagnetic or piezoelectric actuator (e.g., haptic motor 348), for generating vibrations to provide haptic feedback to the user.

Figure 15:
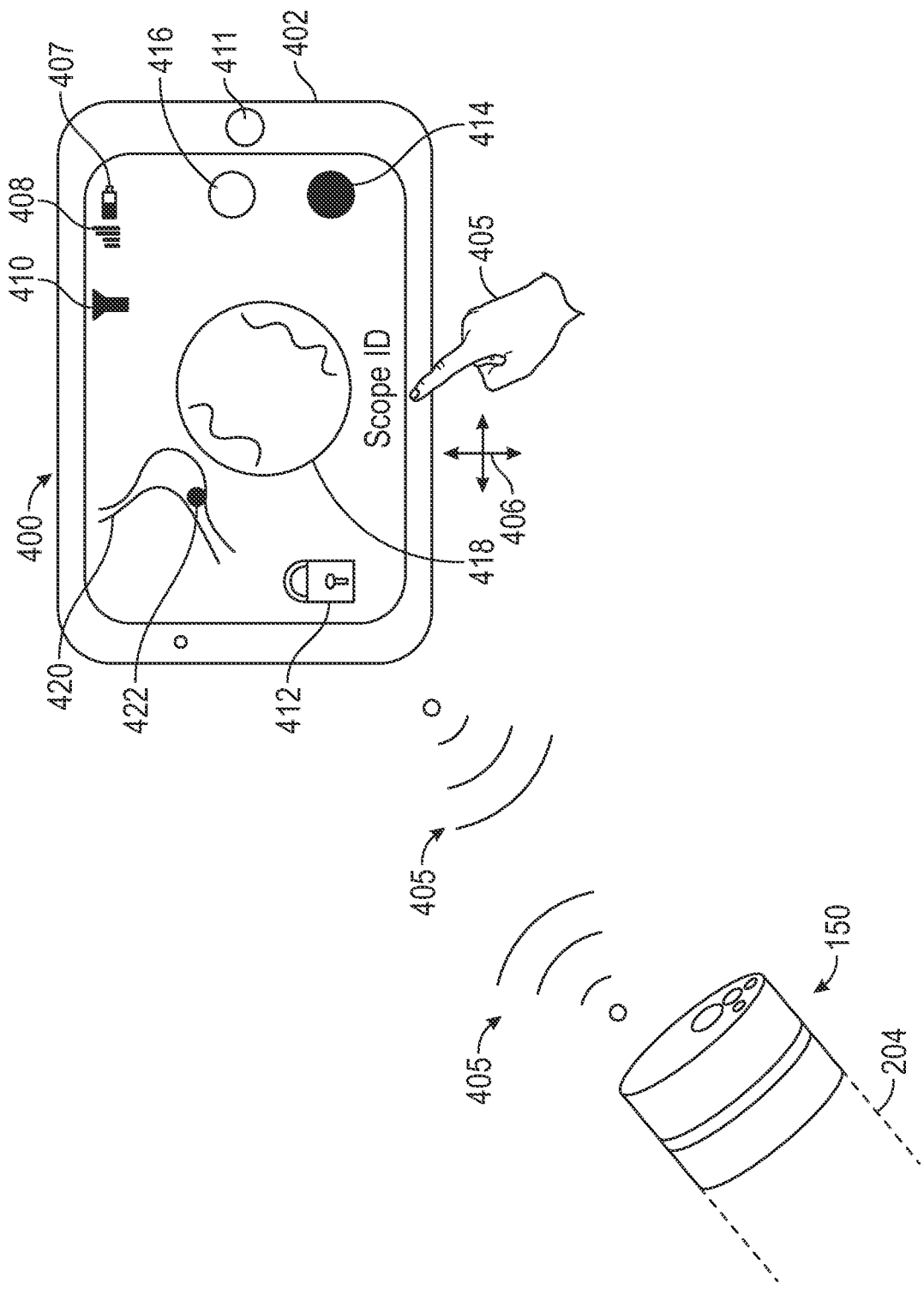
FIG. 15 is a schematic illustration of a navigation and control module for controlling the modular endoscope of FIG. 5 according to another example.

FIG. 15 is a schematic illustration of navigation and control module 400 according to another example for controlling modular endoscope 100 of FIG. 2 according to another example. Navigation and control module 400 can be particularly suitable in instances where endoscopy system 10 includes a motorized drive (e.g., the motorized drive disclosed in the aforementioned PCT Pub. No. WO 2011/140118 A1 to Frassica et al.) and camera module 150 is self-contained, for instance as shown in FIGS. 6-12B, though navigation and control module 400 shown in FIG. 15 can be used for many conventional endoscopy systems.

Navigation and control module 400 can comprise a touchscreen display comprising housing 402 and touchscreen 404. Control module 400 can include a wireless communication device to facilitate wireless communication 405 with camera module 150 of module endoscope 100 and one or more systems, such as, a motorized driver for self-advancement of endoscope 100 upon receiving instructions from the operator 405, provided by one or more "gestures" 406 on touchscreen 404.

The operator can interact with touchscreen 404 to send instructions to endoscope 100, including camera module 150, for the performance of one or more endoscopy functions. For instance, the operator can interact with touchscreen 404 the endoscope using one or more gestures provided on the touchscreen display, including, "pan" gesture (horizontal or vertical direction). Upon receiving the gesture, touchscreen 404 can communicate with imaging and control system 12 (e.g., including drive motor 46) to start advancing the endoscope in a direction corresponding to the movement of the operator's finger, provided during the finger gesture. Additionally, "pinch" to zoom and "tap" to focus gestures can be used.

Control module 400 can be programmed so that touchscreen 404 can display one or more indicators or interface icons. In the illustrated example, touchscreen 404 can display battery icon 407, wireless toggle 408, power toggle 411, angulation lock toggle 412, illumination toggle 410, video record toggle 414 and still image toggle 416. Touchscreen 404 can also display navigation aids, such as imaging unit field of view 418 and anatomy diagram 420 with camera location indicator 422.

The operator can communicate with imaging and control system 12 (e.g., a motorized lens assembly for the objective lens) by tapping on touchscreen 404, to focus or refocus on an anatomical region. The operator can tap once on the "endoscope imaging unit: field of view" button 418 shown in FIG. 15. The gesture can be communicated (wired or wireless communication) to an imaging unit, such as imaging unit 166 (FIG. 6B). The imaging unit can include imaging optics (e.g., lens and prism assemblies) provided on a movable housing, which can be moved, for instance by a motorized driver. In such cases, the "tap" gesture can be converted to instructions for actuating the movable imaging optics, to focus on a region or refocus on the same region or a near-by region (subsequent tapping gesture). In the alternative, the imaging optics can include "zoom lenses" which can zoom in response to the tap gesture.

Other gestures can include tapping on the "record video" toggle 414, tapping on "record still image" toggle 416 to take a single image of the endoscope field of view, press and hold on "record still image" toggle 416 to take a screen shot of the current screen for medical records, or to take a series of shots. In addition, gestures can include tapping on various regions of the interactive graphical user interface, such as angulation toggle 412 for angulation lock, adjusting intensity of light output provided by illumination module 168 using illumination toggle 410, and toggle wireless communication on/off with wireless toggle 408, etc.

Touchscreen 404 can include an interactive graphical user interface, enabling the operator to receive different types of data (e.g., scope specifications such as serial number, type, manufacturer, etc., location of the camera module overlaid on an anatomy map) battery power left on the camera module and the like). Anatomy diagram 420 can be provided by medical imaging uploaded to control module 400 or can comprise generic anatomical diagrams to generally indicate the shape of the anatomy. Location indicator 422 can be provided by a locator provided on wireless camera module 150, such as a locator useable with a surgical tracking system or one that can triangulate the position of camera module 150 within a tracking field.

Figure 16:
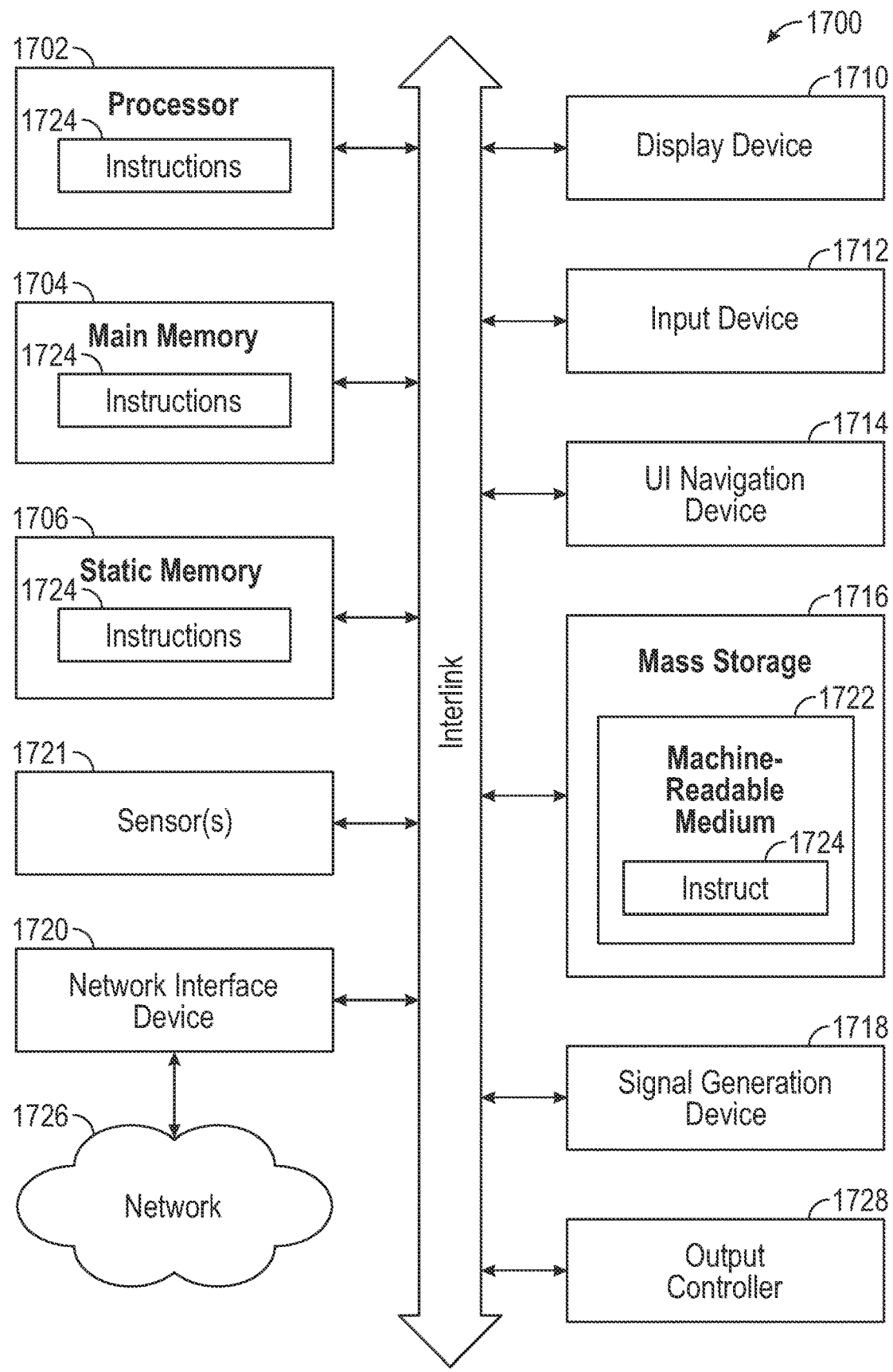
FIG. 16 is a block diagram of an example machine configured as the navigation and control module of FIG. 15 and upon which any one or more of the techniques discussed herein can be performed and with which any of the devices discussed herein can be used.

FIG. 16 illustrates a block diagram of an example machine 1700 configured as the navigation and control module 400 of FIG. 15 and upon which any one or more of the techniques discussed herein can be performed and with which any of the devices discussed herein can be used. For example, machine 1700 can comprise a computing system, including a computing system connected to imaging and control system 12 of FIG. 1. Machine 1700 can comprise an example of a controller for endoscopy system 10. As such instructions 1724 can be executed by processor 1702 to control modular camera module 150. Information regarding the operation of battery icon 407, wireless toggle 408, power toggle 411, angulation lock toggle 412, illumination toggle 410, video record toggle 414, still image toggle 416, imaging unit field of view 418 and anatomy diagram 420 with camera location indicator 422 can be stored in main memory 1704 and accessed by processor 1702. Main memory 1704 can also include instructions for operating wireless camera module 150 based on gestures executed on touchscreen 404. Main memory 1704 can additionally include inventory information for manufacturers and healthcare facilitators of modular endoscope components so as to provide validation functionality of the modular components. Main memory 1704 can additionally include anatomic information for particular patients, such as medical image files.

In alternative examples, machine 1700 can operate as a standalone device or can be connected (e.g., networked) to other machines. In a networked deployment, machine 1700 can operate in the capacity of a server machine, a client machine, or both in server-client network environments. In an example, machine 1700 can act as a peer machine in peer-to-peer (P2P) (or other distributed) network environment. Machine 1700 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 1700 can include hardware processor 1702 (e.g., a central processing unit (CPU), a graphics processing unit (GPU), a hardware processor core, or any combination thereof), main memory 1704 and static memory 1706, some or all of which can communicate with each other via interlink (e.g., bus) 1708. Machine 1700 can further include display unit 1710, alphanumeric input device 1712 (e.g., a keyboard), and user interface (UI) navigation device 1714 (e.g., a mouse). In an example, display unit 1710, input device 1712 and UI navigation device 1714 can be a touch screen display. Machine 1700 can additionally include storage device (e.g., drive unit) 1716, signal generation device 1718 (e.g., a speaker), network interface device 1720, and one or more sensors 1721, such as a global positioning system (GPS) sensor, compass, accelerometer, or other sensor. Machine 1700 can include output controller 1728, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.). Input device 1712 can include wireless toggle 408, power toggle 411, angulation lock toggle 412, illumination toggle 410, video record toggle 414 and still image toggle 416. Output controller 1728 can control operation of motors for advancement of insertion section module 104 as described herein. Display unit 1710 can comprise touchscreen 404. Sensors 1721 can comprise force sensors for sensing the advancement of insertion section module 104. Sensors 1721 can also comprise locations sensors from wireless camera module 150.

Storage device 1716 can include machine readable medium 1722 on which is stored one or more sets of data structures or instructions 1724 (e.g., software) embodying or utilized by any one or more of the techniques or functions described herein. Instructions 1724 can also reside, completely or at least partially, within main memory 1704, within static memory 1706, or within hardware processor 1702 during execution thereof by machine 1700. In an example, one or any combination of hardware processor 1702, main memory 1704, static memory 1706, or storage device 1716 can constitute machine readable media.

While machine readable medium 1722 is illustrated as a single medium, the term "machine readable medium" can include a single medium or multiple media (e.g., a centralized or distributed database, and/or associated caches and servers) configured to store the one or more instructions 1724. The term "machine readable medium" can include any medium that is capable of storing, encoding, or carrying instructions for execution by machine 1700 and that cause machine 1700 to perform any one or more of the techniques of the present disclosure, or that is capable of storing, encoding or carrying data structures used by or associated with such instructions. Non-limiting machine readable medium examples can include solid-state memories, and optical and magnetic media.

Instructions 1724 can further be transmitted or received over communications network 1726 using a transmission medium via network interface device 1720 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, network interface device 1720 can include one or more physical jacks (e.g., Ethernet, coaxial, or phone jacks) or one or more antennas to connect to communications network 1726. In an example, network interface device 1720 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by machine 1700, and includes digital or analog communications signals or other intangible medium to facilitate communication of such software. Interface device 1720 can be configured to communicate with wireless communication circuit 162 of camera module 150, wireless communication unit 172 of control unit 16, a wireless communication unit of insertion section module 104, wireless communication unit 344 and other wireless communication devices described herein.

Figure 17:
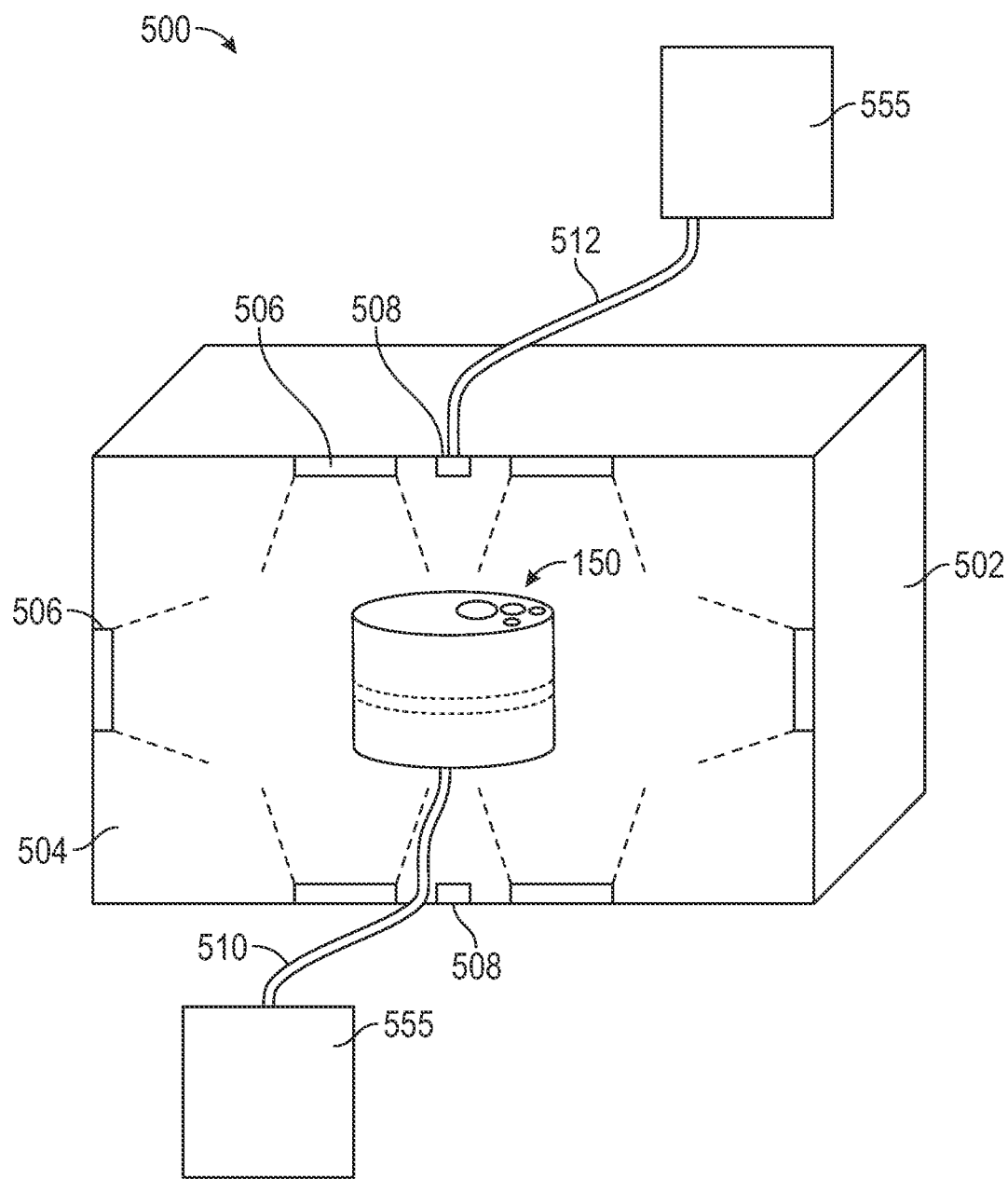
FIG. 17 is a schematic illustration of a sterilization apparatus for sterilizing the camera modules according to the present disclosure.

FIG. 17 is a schematic illustration of sterilization apparatus 500 for sterilizing the camera modules according to the present disclosure, including camera module 150. Sterilization apparatus 500 can comprise housing 502, access panel 504, light sources 506, fluid nozzles 508, power cable 510 and fluid cable 512. Power cable 510 can connect to power source 514 and fluid cable 512 can connect to fluid source 516. Sterilization apparatus 500 can be used for sterilizing camera module 150 prior to reuse after a single use. Sterilization apparatus 500 can include one or more UV light sources 506 and optionally, one or more fluid nozzles 508 that can supply a jet of fluid (water, cleaning detergent, and the like) at high pressures and high temperatures suitable for cleaning camera module 150 prior to reuse. The sterilization process can be controlled to achieve a desired degree of sterilization to reduce any biological substances to comply with standards (e.g., supplied by regulatory authorities such as Food and Drug Administration.) Camera module 150 and controller 400 can be configured to withstand the pressures and temperatures generated by sterilization apparatus 500. Sterilization apparatus 500 can be operated at a medical facility, such as a hospital.

Examples disclosed herein can result in many advantages, including a modular construction, improved ergonomics, and self-contained camera modules for an endoscope.

Figure 18:
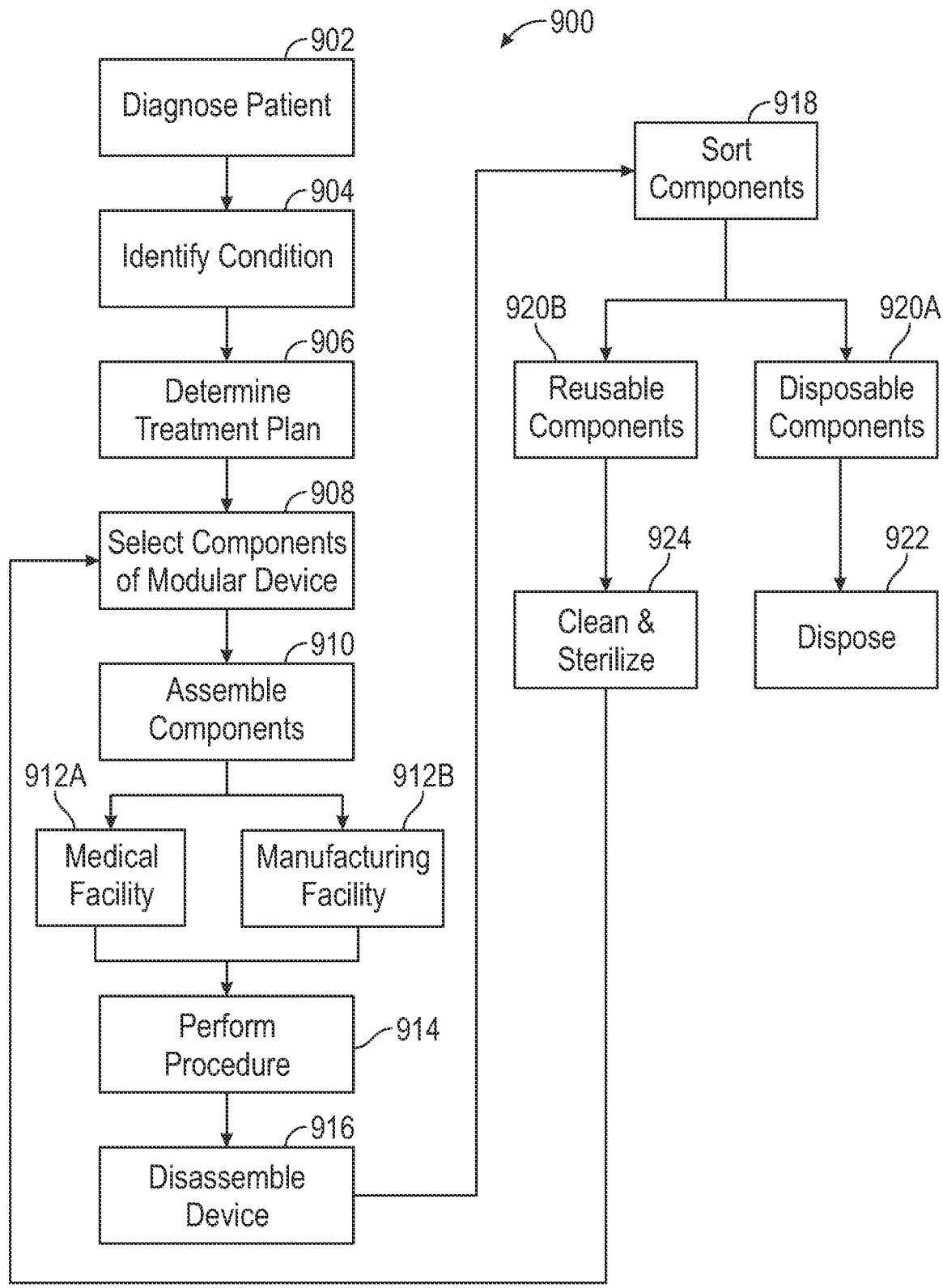
FIG. 18 is a block diagram illustrating a method of processing modular endoscope components for performing one or more surgical procedures.

FIG. 18 is a block diagram illustrating method 900 of processing modular endoscope components for performing a surgical procedure. At step 902, a specific patient can be diagnosed as having a particular condition or as needing a particular evaluation. A surgeon or other qualified medical professional can perform the diagnosis.

At step 904, a particular condition of the patient can be identified as needing interaction from a particular therapy or evaluative procedure. For example, a particular organ or anatomic region can be identified as needing a specific intervention or evaluation.

At step 906, a particular treatment plan can be developed to address the condition identified at step 904. The treatment plan can include selection of a therapy to be performed, such as ablation, freezing, cauterizing, cutting, attaching and the like. The treatment plan can also include a plan for performing a surgical technique, such as instructions for delivering the selected therapy to the particular organ or anatomic regions, such as by using a camera-enabled endoscope.

At step 908, components of a medical device to deliver the selected therapy can be selected. For example, a particular treatment module can be selected to provide the selected therapy, a particular sheath or shaft can be selected to deliver the treatment module, and a particular control module can be selected to control operation of the modular medical device. Features and characteristics of the selected sheath or shaft can be selected, such as the number of delivery lumens needed to provide the treatment, guidance and steering capabilities needed for the selected treatment plan and therapy. Likewise, a camera module and a control module can be selected to facilitate guiding of the treatment module and viewing of the anatomic region or organ.

At step 910, the selected components of step 908 can be assembled. The selected components can be assembled at a medical facility where the procedure is to be performed, at step 912A. For example, the modular components can be user-assembled. In particular, a camera module can be attached using an attachment mechanism, such as one of the attachment devices described herein, e.g., attachment devices 200, 220, 240, 260 and 280. Additionally, a control module can be selected, such as module 300 or module 400. The selected components can be assembled at a manufacturing facility, at step 912B.

At step 914, the procedure planned for at step 906 can be performed with the medical device assembled at step 910.

At step 916, the assembled medical device used in the procedure at step 914 can be disassembled. The medical device can be disassembled at the medical facility of step 912A or can be sent offsite to be disassembled at the manufacturing facility of step 912B or another repurposing facility. The modular components can be user-disassembled by operating an attachment mechanism.

At step 918, the disassembled components can be sorted into components that can be disposed of at step 920A and components that can be reused at step 920B.

At step 922, the disposable components can be disposed of, such as by being destroyed or discarded. The disposable components can comprise a disposable insertion sheath.

At step 924, the reusable components of step 920B can be cleaned and sterilized for reuse. The reusable components can comprise a detachable camera module and a detachable control module. As such, the cleaned and sterilized components can be returned to inventory of the medical facility or manufacturing facility to be used in additional procedures. In examples, camera module 150 and control module 300 can be cleaned and sterilized using sterilization apparatus 500.

VARIOUS NOTES & EXAMPLES

Example 1 can include or use subject matter such as a modular endoscopy system that can comprise a first modular section comprising an imaging unit and an illumination unit and a second modular section user-detachably connectable to the first modular section via an attachment mechanism, the second modular section being patient insertable, wherein the first modular section is positionable at a distal end section of the second modular section and is configured to illuminate and image a portion of a patient anatomy.

Example 2 can include, or can optionally be combined with the subject matter of Example 1, to optionally include a second modular section that includes an insertion section module comprising an elongate working section.

Example 3 can include, or can optionally be combined with the subject matter of one or any combination of Examples 1 or 2 to optionally include a third modular section that is user-detachably connectable to the second modular section.

Example 4 can include, or can optionally be combined with the subject matter of one or any combination of Examples 1 through 3 to optionally include a third modular section that can comprise a navigation and control module operatively connectable to the elongate working section.

Example 5 can include, or can optionally be combined with the subject matter of one or any combination of Examples 1 through 4 to optionally include a distal end section of the second modular section that can comprise an elevator mechanism configured to orient and support one or more therapeutic tools extended through the second modular section.

Example 6 can include, or can optionally be combined with the subject matter of one or any combination of Examples 1 through 5 to optionally include an elevator mechanism that can be fluidly isolated from the first modular section and the third modular section.

Example 7 can include, or can optionally be combined with the subject matter of one or any combination of Examples 1 through 6 to optionally include a first modular section that can further comprise a rechargeable power source configured to provide power to an imaging unit and the illumination unit of the first modular section.

Example 8 can include, or can optionally be combined with the subject matter of one or any combination of Examples 1 through 7 to optionally include a first modular section that can further comprise a wireless communication circuit, configured to send or receive data or instructions from the second modular section, or an imaging and control system.

Example 9 can include, or can optionally be combined with the subject matter of one or any combination of Examples 1 through 8 to optionally include, when attached, a first modular section and a second modular section that are generally co-axially positioned along a longitudinal axis of the second modular section.

Example 10 can include, or can optionally be combined with the subject matter of one or any combination of Examples 1 through 9 to optionally include, when attached, a first modular section that is radially offset from a longitudinal axis of the second modular section.

Example 11 can include, or can optionally be combined with the subject matter of one or any combination of Examples 1 through 10 to optionally include an attachment mechanism that comprises a retention band.

Example 12 can include, or can optionally be combined with the subject matter of one or any combination of Examples 1 through 11 to optionally include a retention band comprising a clasp.

Example 13 can include, or can optionally be combined with the subject matter of one or any combination of Examples 1 through 12 to optionally include a retention band comprising a resilient material.

Example 14 can include, or can optionally be combined with the subject matter of one or any combination of Examples 1 through 13 to optionally include an attachment mechanism comprising a resilient clip.

Example 15 can include, or can optionally be combined with the subject matter of one or any combination of Examples 1 through 14 to optionally include an attachment mechanism comprising a plurality of resilient clips mounted to a base.

Example 16 can include, or can optionally be combined with the subject matter of one or any combination of Examples 1 through 15 to optionally include an attachment mechanism comprising a hinged basket.

Example 17 can include, or can optionally be combined with the subject matter of one or any combination of Examples 1 through 16 to optionally include a hinged basket comprising a fixed jaw coupled to the distal end section of the second modular section, and a moveable jaw coupled to the fixed jaw.

Example 18 can include, or can optionally be combined with the subject matter of one or any combination of Examples 1 through 17 to optionally include a moveable jaw that is hinged to the fixed jaw at a rotation axis.

Example 19 can include, or can optionally be combined with the subject matter of one or any combination of Examples 1 through 18 to optionally include a moveable jaw that is hinged to the fixed jaw via a plurality of resilient bands.

Example 20 can include, or can optionally be combined with the subject matter of one or any combination of Examples 1 through 19 to optionally include an attachment mechanism that comprises an expandable sleeve.

Example 21 can include, or can optionally be combined with the subject matter of one or any combination of Examples 1 through 20 to optionally include an attachment mechanism that comprises a threaded engagement between the first modular section and the second modular section.

Example 22 can include, or can optionally be combined with the subject matter of one or any combination of Examples 1 through 21 to optionally include a first modular section that comprises first near-field communication device, and a second modular section that comprises a second near-field communication device, wherein near-field communication can be established between the first modular section and the second modular section.

Example 23 can include, or can optionally be combined with the subject matter of one or any combination of Examples 1 through 22 to optionally include a second modular section that includes memory having stored therein one or more of manufacturer information, model number information and serial number information.

Example 24 can include, or can optionally be combined with the subject matter of one or any combination of Examples 1 through 23 to optionally include an attachment mechanism configured to secure the first modular section in an end-viewing orientation.

Example 25 can include, or can optionally be combined with the subject matter of one or any combination of Examples 1 through 24 to optionally include an attachment mechanism configured to secure the first modular section in a side-viewing orientation.

Example 26 can include or use subject matter such as a method of using a modular endoscopy system that can comprise attaching a first modular section of the modular endoscopy system to a second modular section of the modular endoscopy system, positioning at least a portion of the modular endoscopy system within a patient, illuminating and imaging a portion of a patient anatomy via the first modular section, removing the modular endoscopy system from the patient, and detaching the second modular section from the first modular section after removal of the modular endoscopy system from the patient.

Example 27 can include, or can optionally be combined with the subject matter of Example 26, to optionally include assembling the first and second modular components of the modular endoscopy system at a surgical facility.

Example 28 can include, or can optionally be combined with the subject matter of one or any combination of Examples 26 or 27 to optionally include a first modular component that comprises an insertion section module, and a second modular component comprises a camera module.

Example 29 can include, or can optionally be combined with the subject matter of one or any combination of Examples 26 through 28 to optionally include disposing of the insertion section module, and cleaning and sanitizing the camera module.

Example 30 can include, or can optionally be combined with the subject matter of one or any combination of Examples 26 through 29 to optionally include cleaning and sanitizing the camera module by positioning the camera module within a sterilization apparatus comprising an enclosure having an ultraviolet light source and a fluid jet.

Example 31 can include, or can optionally be combined with the subject matter of one or any combination of Examples 26 through 30 to optionally include reusing the cleaned and sanitized reusable components in a subsequent medical procedure.

Example 32 can include, or can optionally be combined with the subject matter of one or any combination of Examples 26 through 31 to optionally include positioning at least the portion of the modular endoscopy system within the patient by inserting a portion of the insertion section module into the patient to position the camera module adjacent anatomy to be imaged.

Example 33 can include, or can optionally be combined with the subject matter of one or any combination of Examples 26 through 32 to optionally include establishing a near-field communication link between the first modular section and the second modular section.

Example 34 can include, or can optionally be combined with the subject matter of one or any combination of Examples 26 through 33 to optionally include a second modular section that includes memory having stored therein one or more of manufacturer information, model number information and serial number information.

Example 35 can include, or can optionally be combined with the subject matter of one or any combination of Examples 26 through 34 to optionally include identifying a specific treatment for the patient, and selecting the first modular section capable of treating the patient with the identified treatment.

Example 36 can include or use subject matter such as an insertion section module for an endoscope that can comprise a shaft comprising a flexible, elongate body extending from a proximal end to a distal end, and a coupling mechanism located proximal the distal end, the coupling mechanism configured to releasably secure a camera module to the insertion section module.

Example 37 can include, or can optionally be combined with the subject matter of Example 36, to optionally include an attachment mechanism that comprises a retention band.

Example 38 can include, or can optionally be combined with the subject matter of one or any combination of Examples 36 or 37 to optionally include a retention band comprising a clasp.

Example 39 can include, or can optionally be combined with the subject matter of one or any combination of Examples 36 through 38 to optionally include a retention band comprising a resilient material.

Example 40 can include, or can optionally be combined with the subject matter of one or any combination of Examples 36 through 39 to optionally include an attachment mechanism that comprises a resilient clip.

Example 41 can include, or can optionally be combined with the subject matter of one or any combination of Examples 36 through 40 to optionally include an attachment mechanism that comprises a plurality of resilient clips mounted to a base.

Example 42 can include, or can optionally be combined with the subject matter of one or any combination of Examples 36 through 41 to optionally include an attachment mechanism that comprises a hinged basket.

Example 43 can include, or can optionally be combined with the subject matter of one or any combination of Examples 36 through 42 to optionally include a hinged basket that comprises a fixed jaw coupled to the distal end section of the second modular section, and a moveable jaw coupled to the fixed jaw.

Example 44 can include, or can optionally be combined with the subject matter of one or any combination of Examples 36 through 43 to optionally include a moveable jaw that is hinged to the fixed jaw at a rotation axis.

Example 45 can include, or can optionally be combined with the subject matter of one or any combination of Examples 36 through 44 to optionally include a moveable jaw that is hinged to the fixed jaw via a plurality of resilient bands.

Example 46 can include, or can optionally be combined with the subject matter of one or any combination of Examples 36 through 45 to optionally include an attachment mechanism that comprises an expandable sleeve.

Example 47 can include, or can optionally be combined with the subject matter of one or any combination of Examples 36 through 46 to optionally include an attachment mechanism that comprises a threaded engagement between the first modular section and the second modular section.

Example 48 can include or use subject matter such as a method of assembling a modular endoscopy system that can comprise bringing the first modular section of the modular endoscopy system proximate to a second modular section of the modular endoscopy system, the first modular section and the second modular section each comprising a near-field communication chip, establishing near-field communication between the first modular section and the second modular section when the first modular section and the second modular section are in a detached state, to validate the second modular section, and attaching the first modular section to the second modular section.

Example 49 can include, or can optionally be combined with the subject matter of Example 48, to optionally include transmitting, via one or more wireless communication circuits provided on the first communication module, identification data read from the second modular section while validating the second modular section, to be displayed on a display along with images collected by the imaging unit of the first modular section.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of using a modular endoscopy system, the method comprising:
   attaching a first modular section of the modular endoscopy system to a second modular section of the modular endoscopy system using an attachment mechanism;
   positioning at least a portion of the modular endoscopy system within a patient;
   illuminating and imaging a portion of a patient anatomy via the first modular section;
   removing the modular endoscopy system from the patient; and
   detaching the second modular section from the first modular section after removal of the modular endoscopy system from the patient;
   wherein the attachment mechanism comprises a retention band comprising first and second ends extending from a distal end face of the second modular section.

2. The method of claim 1, further comprising assembling the first modular section and the second modular section of the modular endoscopy system at a surgical facility.

3. The method of claim 1, wherein:
   the first modular section comprises a camera module; and
   the second modular section comprises an elongate working section.

4. The method of claim 3, further comprising disposing of the elongate working section via destroying the elongate working section.

5. The method of claim 3, further comprising cleaning and sanitizing the camera module.

6. The method of claim 5, wherein the cleaning and sanitizing the camera module comprises positioning the camera module within a sterilization apparatus comprising an enclosure having an ultraviolet light source and a fluid jet.

7. The method of claim 5, further comprising reusing the camera module in a subsequent medical procedure.

8. The method of claim 3, wherein the camera module comprises:
   a housing in which an imaging unit and an illumination unit are disposed, the housing comprising:
       a first shell comprising:
           a first end face that is flat and circular; and
           a first circular sidewall circumscribing the first end face; and
       a second shell separable from the first shell, the second shell comprising:
           a second end face that is flat and circular; and
           a second circular sidewall circumscribing the second end face;
       a mechanical coupling for joining the first shell and the second shell; and
       a groove circumscribing one or both of the first circular sidewall and the second circular sidewall.

9. The method of claim 8, further comprising a seal positioned between the first shell and the second shell.

10. The method of claim 8, wherein the housing comprises a passage extending between the first end face and the second end face to allow irrigation fluid to pass through the housing isolated from the imaging unit and the illumination unit.

11. The method of claim 8, wherein the housing comprises lenses located on one of the first end face and the second end face to allow for passage of light to the imaging unit and the illumination unit.

12. The method of claim 8, wherein the housing is fabricated from transparent material.

13. The method of claim 8, wherein the attachment mechanism is configured to secure the first modular section in a side-viewing orientation such that the first modular section is disposed within a radial boundary of a distal end face of the second modular section and a central axis of the first end face and the second end face of the second modular section is parallel to a central axis of the second modular section.

14. The method of claim 1, wherein positioning at least the portion of the modular endoscopy system within the patient comprises inserting a portion of the second modular section into the patient to position the first modular section adjacent to anatomy to be imaged.

15. The method of claim 1, wherein the first modular section further comprises a rechargeable power source configured to provide power to an imaging unit and an illumination unit of the first modular section.

16. The method of claim 1, wherein a distal end section of the second modular section comprises an elevator mechanism configured to orient and support one or more therapeutic tools extended through the second modular section, wherein the first modular section is distal of the elevator mechanism of the second modular section.

17. The method of claim 1, further comprising:
a third modular section, the third modular section being user-detachably connectable to the second modular section.

18. The method of claim 17, wherein the third modular section comprises a navigation and control module operatively connectable to the second modular section, the navigation and control module comprising a handle that is user-detachably connectable to the second modular section.

19. The method of claim 1, wherein the attachment mechanism is configured to secure the first modular section in an end-viewing orientation such that the first modular section is disposed within a radial boundary of the distal end face of the second modular section.

20. The method of claim 1, further comprising establishing a near-field communication link between the first modular section and the second modular section.

21. The method of claim 1, wherein the second modular section includes memory having stored therein one or more of manufacturer information, model number information and serial number information.

22. The method of claim 1, wherein the retention band comprises a resilient material.

23. The method of claim 1, further comprising:
identifying a specific treatment for the patient, the specific treatment being selected from a group consisting of a biopsy and a therapy for a disease; and
selecting the first modular section to be capable of treating the patient with the identified specific treatment.

* * * * *